(12) United States Patent
Shikata

(10) Patent No.: US 10,687,783 B2
(45) Date of Patent: Jun. 23, 2020

(54) PUNCTURE ADAPTER, ULTRASOUND PROBE, AND ULTRASOUND DIAGNOSTIC APPARATUS

(71) Applicant: TOSHIBA MEDICAL SYSTEMS CORPORATION, Otawara-Shi (JP)

(72) Inventor: Hiroyuki Shikata, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 1284 days.

(21) Appl. No.: 14/820,083

(22) Filed: Aug. 6, 2015

(65) Prior Publication Data
US 2015/0335350 A1 Nov. 26, 2015

Related U.S. Application Data

(63) Continuation of application No. PCT/JP2014/052688, filed on Feb. 5, 2014.

(30) Foreign Application Priority Data

Feb. 6, 2013 (JP) .................................. 2013-021578

(51) Int. Cl.
*A61B 8/08* (2006.01)
*A61B 8/14* (2006.01)
(Continued)

(52) U.S. Cl.
CPC .............. *A61B 8/0841* (2013.01); *A61B 8/14* (2013.01); *A61B 8/4444* (2013.01);
(Continued)

(58) Field of Classification Search
CPC ... A61B 8/0841; A61B 8/4444; A61B 8/4422; A61B 8/4455; A61B 90/11;
(Continued)

(56) References Cited

U.S. PATENT DOCUMENTS 5,235,987 A * 8/1993 Wolfe .................. A61B 8/0833
600/461

FOREIGN PATENT DOCUMENTS

JP 10-248849 A 9/1998
JP 2006-020890 A 1/2006
(Continued)

OTHER PUBLICATIONS

Machine translation of JPO Pub. No. JP 2011152295 A, Aug. 11, 2011.*

(Continued)

*Primary Examiner* — Carolyn A Pehlke
(74) *Attorney, Agent, or Firm* — Oblon, McClelland, Maier & Neustadt, L.L.P.

(57) ABSTRACT

A puncture adapter according to the embodiment includes a first pressing part that has a first surface and a second surface serving as a surface opposite to the first surface; a second pressing part that has a third surface; a fixing part that fixes, when a probe body is covered with a cover, the first pressing part and the second pressing part to the probe body with the cover interposed between a cutout surface of a cutout portion of the probe body and the first surface of the first pressing part and with the third surface of the second pressing part brought into contact with the second surface of the first pressing part; and a guide groove that guides a puncture needle, and is formed on at least one of the second surface of the first pressing part and the third surface of the second pressing part.

16 Claims, 31 Drawing Sheets

(51) Int. Cl.
  *A61B 17/34* (2006.01)
  *A61B 8/00* (2006.01)
  *A61B 90/11* (2016.01)
  *A61B 90/00* (2016.01)

(52) U.S. Cl.
  CPC ........ *A61B 8/5207* (2013.01); *A61B 17/3403* (2013.01); *A61B 90/11* (2016.02); *A61B 8/4411* (2013.01); *A61B 8/4422* (2013.01); *A61B 8/4455* (2013.01); *A61B 8/488* (2013.01); *A61B 2017/3413* (2013.01); *A61B 2090/378* (2016.02)

(58) Field of Classification Search
  CPC ............ A61B 17/3403; A61B 17/3411; A61B 17/3413; A61B 17/3405
  See application file for complete search history.

(56) References Cited

FOREIGN PATENT DOCUMENTS

| | | |
|---|---|---|
| JP | 2006-212165 A | 8/2006 |
| JP | 2011-152295 A | 8/2011 |

OTHER PUBLICATIONS

International Search Report dated Mar. 11, 2014 in PCT/JP2014/052688 (with English Translation).
Written Opinion dated Mar. 11, 2014 in PCT/JP2014/052688.

\* cited by examiner

ADAPTER SIDE

PROBE BODY SIDE

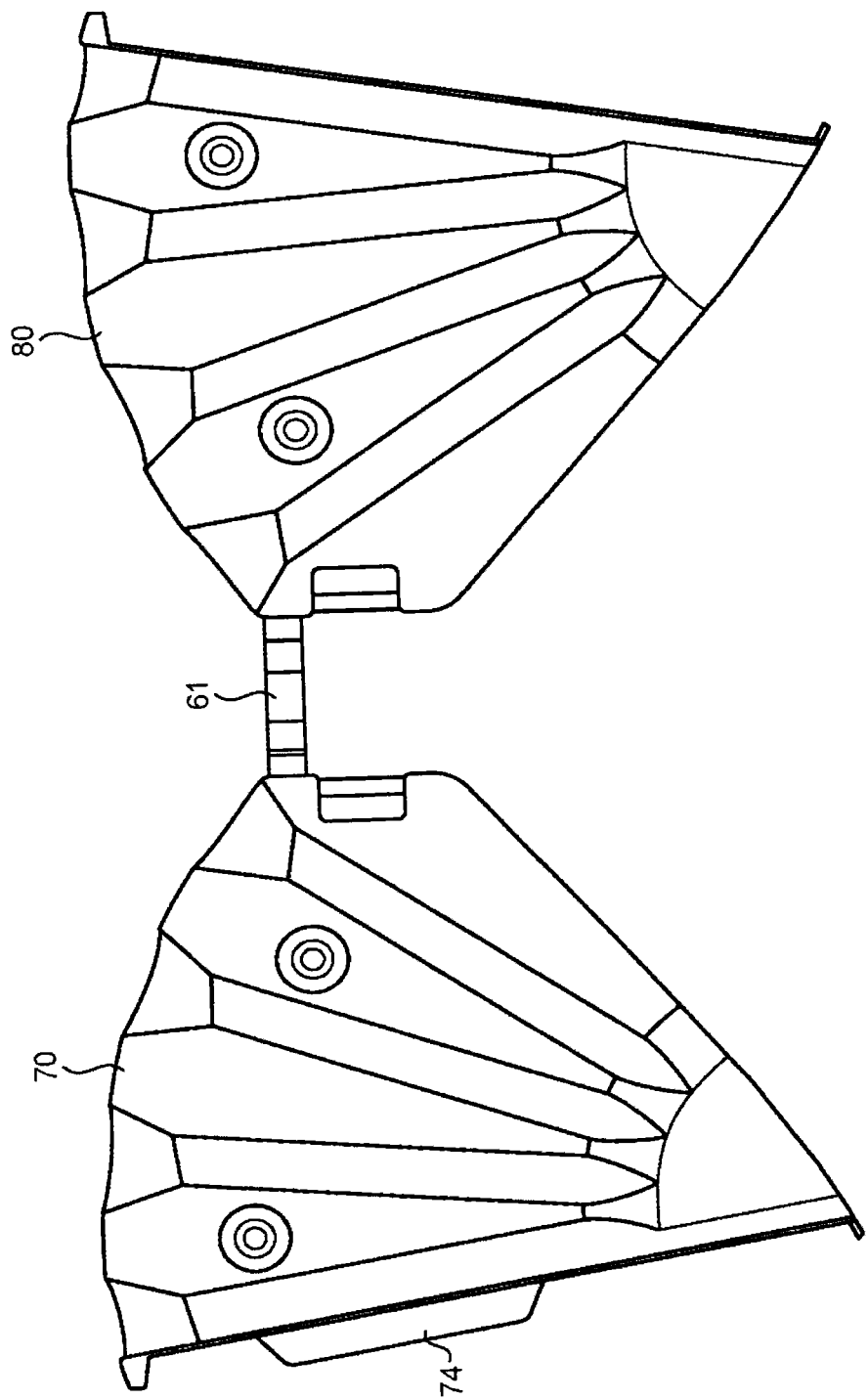

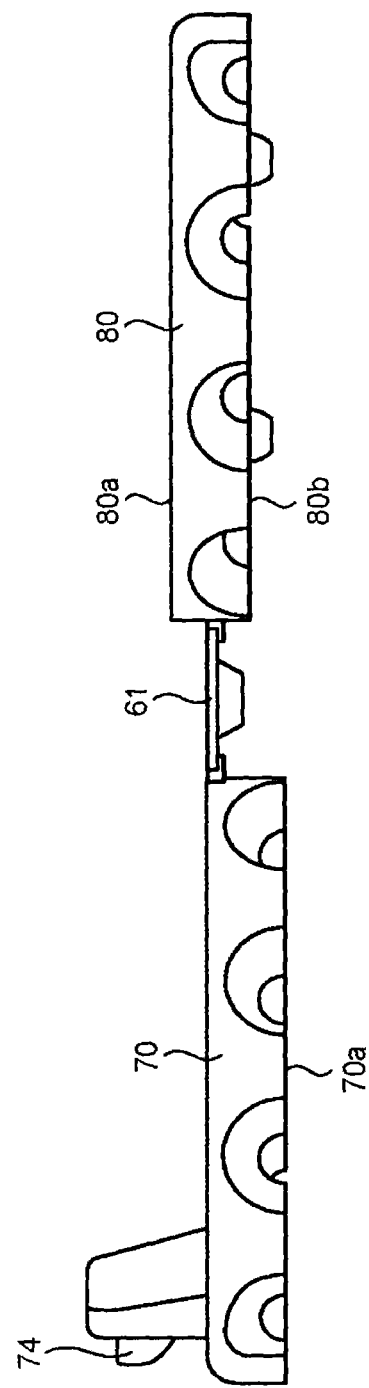

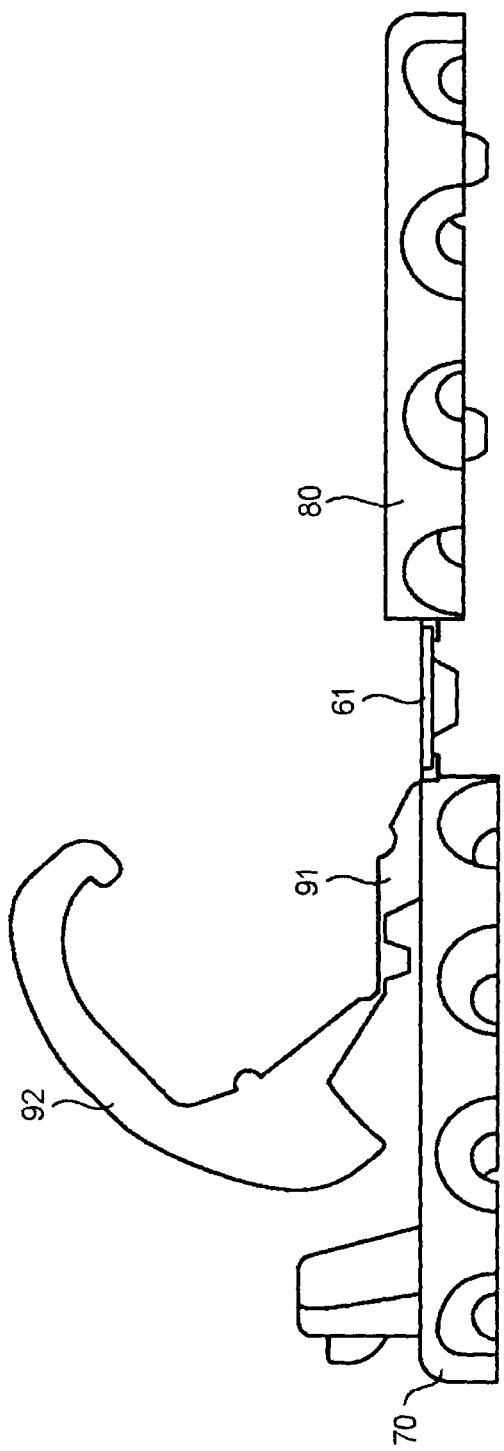

PUNCTURE ADAPTER, ULTRASOUND PROBE, AND ULTRASOUND DIAGNOSTIC APPARATUS

CROSS-REFERENCE TO RELATED APPLICATIONS

This application is a continuation of PCT international application Ser. No. PCT/JP2014/052688 filed on Feb. 5, 2014 which designates the United States, incorporated herein by reference, and which claims the benefit of priority from Japanese Patent Application No. 2013-021578, filed on Feb. 6, 2013, the entire contents of which are incorporated herein by reference.

FIELD

Embodiments described herein relate generally to a puncture adapter, an ultrasound probe, and an ultrasound diagnostic apparatus.

BACKGROUND

Conventionally widely performed are paracenteses in which a puncture needle is inserted into an affected part for removal of an internal tissue, such as a tumor, injection of a liquid medicine, or treatment with external energy, for example. To puncture an object more safely and reliably, an ultrasound-guided paracentesis is useful, in which a puncture is performed while the object of the puncture and a puncture needle are being displayed on an ultrasound tomographic image.

To prevent infection and probe contamination in the puncture, a probe cover may be attached to an ultrasound probe. The probe cover is a bag-shaped product made of an extremely thin rubber or plastic material. The probe cover covers a probe body and a part of a cable that connects the probe body to an ultrasound diagnostic apparatus, thereby covering the probe body. In a case where the probe cover is attached to the ultrasound probe, a puncture adapter is attached from the outside of the probe cover to guide the puncture needle.

The probe cover is fixed to the probe with a cover pressing part alone, for example. To securely fix the probe cover to the probe, the thickness of the cover pressing part is increased to secure the rigidity. This structure may possibly reduce an effective area for transmission and reception of ultrasound waves, resulting in a deteriorated image quality.

BRIEF DESCRIPTION OF THE DRAWINGS

FIG. 9B is another perspective view of the guide part and the pressing part according to the second embodiment;

FIG. 9C is a side view of the guide part and the pressing part viewed from the gripper side according to the second embodiment;

FIG. 11D is yet another perspective view of the fixing part according to the second embodiment;

DETAILED DESCRIPTION

A puncture adapter, an ultrasound probe, and an ultrasound diagnostic apparatus according to embodiments are described below with reference to the accompanying drawings. The ultrasound probe according to the embodiments is a puncture ultrasound probe to which a puncture needle can be attached.

A puncture adapter according to the embodiment includes a first pressing part that has a first surface and a second surface serving as a surface opposite to the first surface; a second pressing part that has a third surface; a fixing part that fixes, when a probe body is covered with a cover, the first pressing part and the second pressing part to the probe body with the cover interposed between a cutout surface of a cutout portion of the probe body and the first surface of the first pressing part and with the third surface of the second pressing part brought into contact with the second surface of the first pressing part; and a guide groove that guides a puncture needle, and is formed on at least one of the second surface of the first pressing part and the third surface of the second pressing part.

First Embodiment

Figure 1:
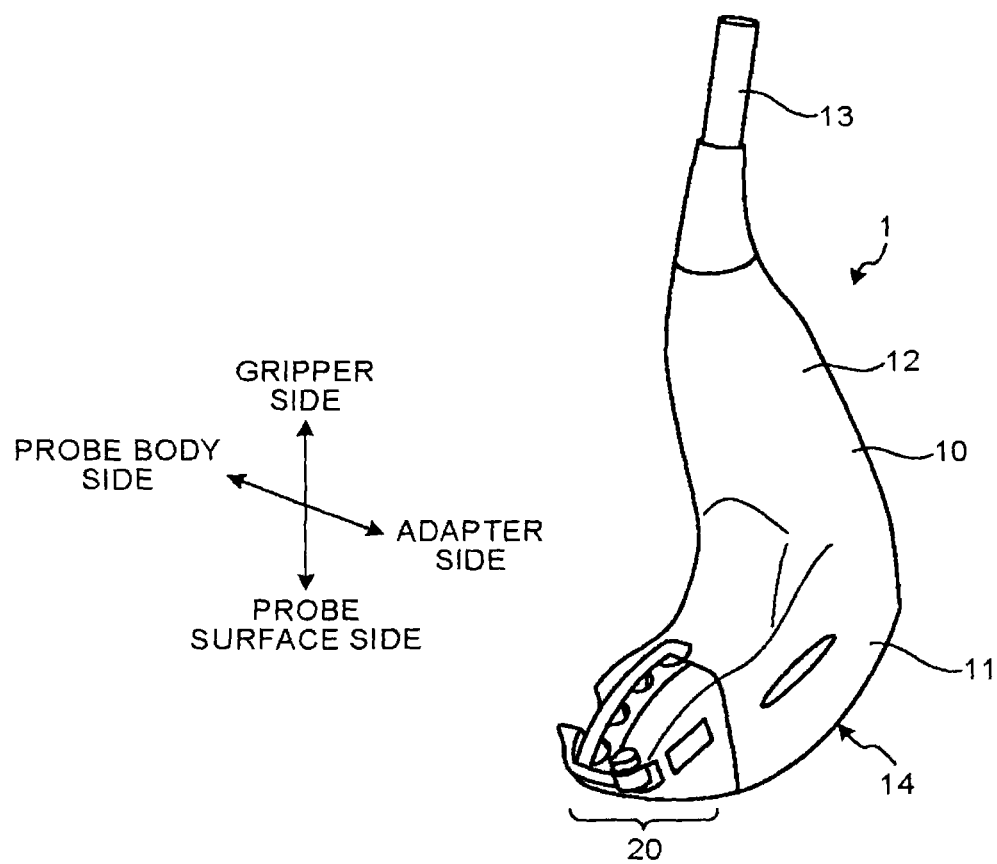
FIG. 1 is a perspective view of an entire configuration of an ultrasound probe according to a first embodiment.

FIG. 1 is a perspective view of an entire configuration of an ultrasound probe 1 according to a first embodiment. As illustrated in FIG. 1, the ultrasound probe 1 includes a probe body 10 and an adapter 20.

The probe body 10 includes ultrasound transducer elements (which will be described later). The probe body 10 further includes a probe part 11, a gripper 12, and a connecting cable 13. The probe part 11 performs ultrasound scanning in the longitudinal direction of a probe surface 14 (also referred to as a radiation surface). The gripper 12 is provided on the side opposite to the probe surface 14 in a manner forming an L-shape the corner of which corresponds to an end of the probe part 11, and is gripped by an operator. The connecting cable 13 is provided to an end of the gripper 12 on the side opposite to the corner of the L-shape. The connecting cable 13 is connected to an ultrasound diagnostic apparatus body, which is not illustrated. The probe body 10 has a cutout portion 15 including a cutout formed at an end of the probe surface 14. The cutout portion 15 is formed at the end of the probe surface 14 on the side opposite to the gripper 12. The adapter 20 is attached to the cutout portion 15. To specify the directions with respect to the ultrasound probe 1, the upper direction in FIG. 1 is referred to as a gripper 12 side direction, and the lower direction is referred to as a probe surface 14 side direction. The right direction in FIG. 1 is referred to as an adapter 20 side direction, and the left direction is referred to as a probe body 10 side direction.

Figure 2:
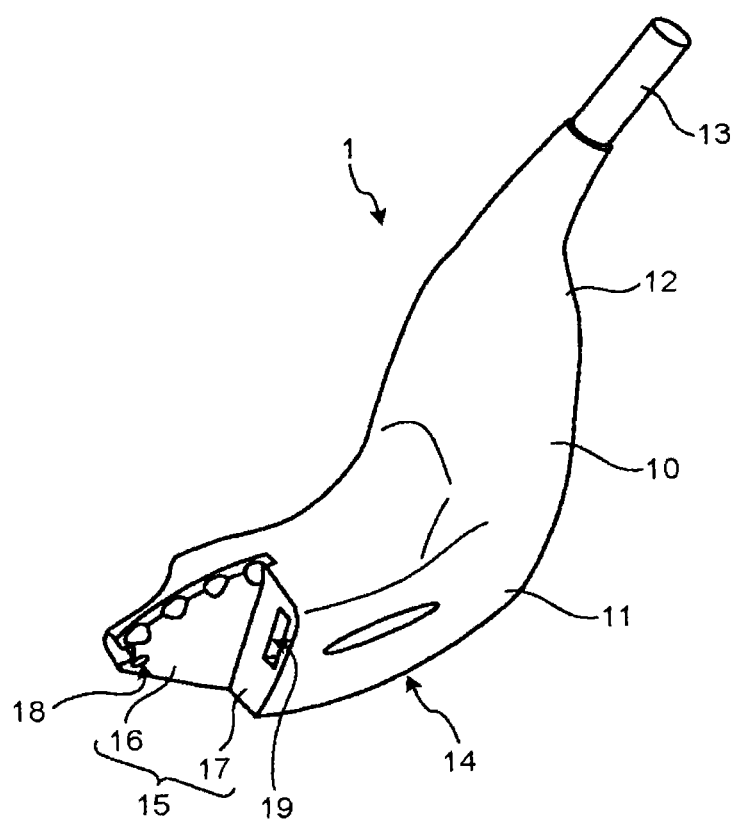
FIG. 2 is a perspective view of an example of a cutout portion according to the first embodiment.

The following describes the cutout portion 15 with reference to FIG. 2. FIG. 2 is a perspective view of an example of the cutout portion 15 according to the first embodiment. As illustrated in FIG. 2, an L-shaped cutout is formed at an end of the probe surface 14. The cutout portion 15 has two surfaces formed along the L-shaped cutout as cutout surfaces. The cutout portion 15, for example, has a first surface 16 and a second surface 17 the respective ends of which are coupled nearly orthogonally. The first surface 16 of the cutout portion 15 sandwiches a part of a cover with a pressing part 40 (also referred to as a first pressing part), which will be described later. The first surface 16 of the cutout portion 15 has a recess 18 that fits onto a protrusion 32 formed on a guide part 30 (also referred to as a second pressing part), which will be described later. The second surface 17 of the cutout portion 15 sandwiches a part of the cover with a surface of the adapter 20 in the short direction. The second surface 17 of the cutout portion 15 has a recess 19 that fits onto a protrusion 52 formed on a fixing part 50, which will be described later.

Figure 3A:
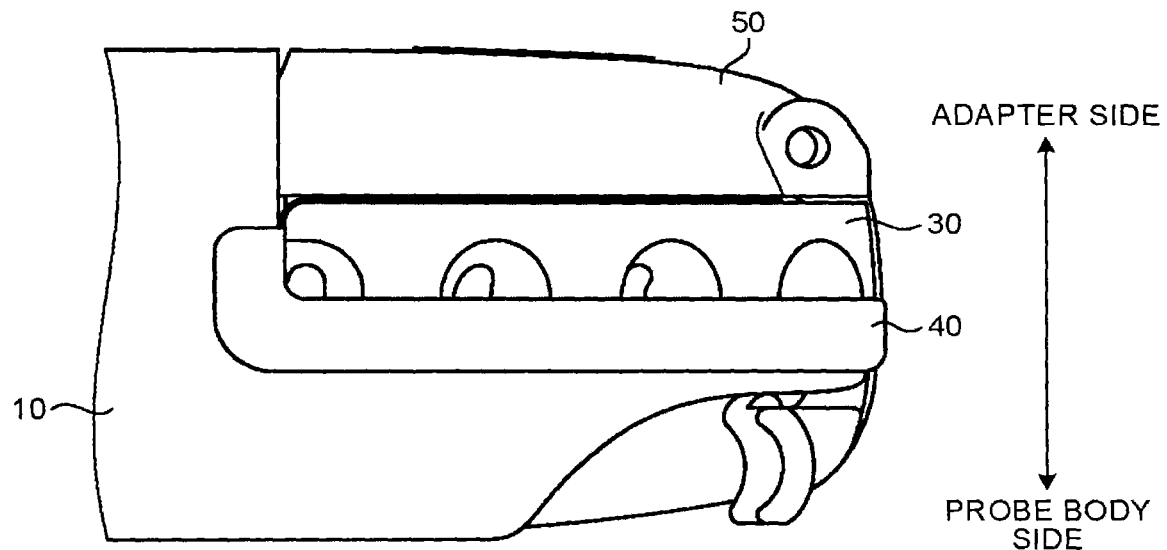
FIG. 3A is a perspective view of an adapter viewed from the gripper side according to the first embodiment.
Figure 3B:
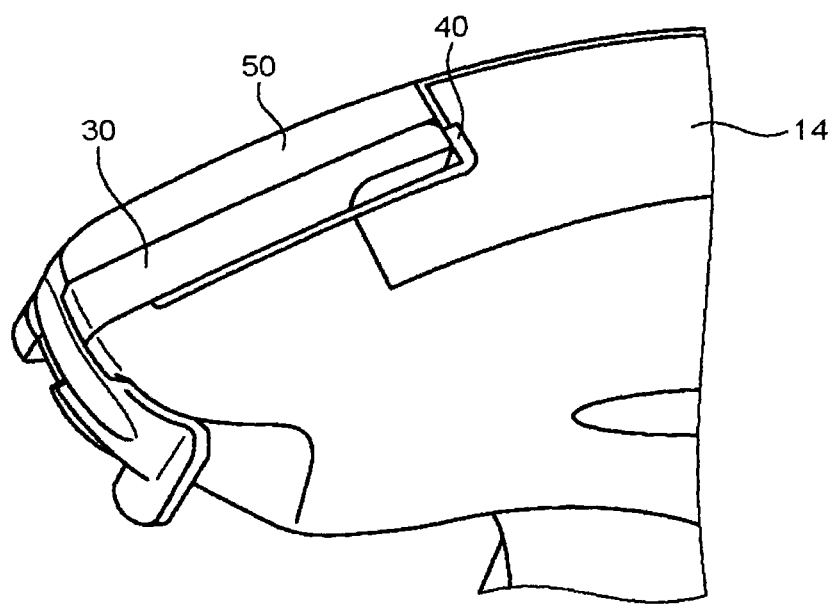
FIG. 3B is a perspective view of the adapter viewed from the probe surface side according to the first embodiment.

Referring back to FIG. 1, the adapter 20 fits into the cutout portion 15 of the probe body 10. In other words, the adapter 20 is detachably attached to the cutout portion 15 of the probe body 10. The following describes the adapter 20 with reference to FIGS. 3A and 3B. FIG. 3A is a perspective view of the adapter 20 viewed from the gripper 12 side according to the first embodiment. FIG. 3B is a perspective view of the adapter 20 viewed from the probe surface 14 side according to the first embodiment.

As illustrated in FIG. 3A, the adapter 20 includes the guide part 30, the pressing part 40, and the fixing part 50. Assuming that the upper direction in FIG. 3A corresponds to the adapter 20 side direction and that the lower direction corresponds to the probe body 10 side direction, the adapter 20 is attached to the cutout portion 15 with the fixing part 50, the guide part 30, and the pressing part 40 arranged in this order from the adapter 20 side to the probe body 10 side.

Assuming that the upper direction in FIG. 3B corresponds to the probe body 10 side direction and that the lower direction corresponds to the adapter 20 side direction, the adapter 20 is attached to the cutout portion 15 with the fixing part 50, the guide part 30, and the pressing part 40 arranged in this order from the probe body 10 side to the adapter 20 side. The guide part 30, the pressing part 40, and the fixing part 50 will be described later in detail.

Figure 4A:
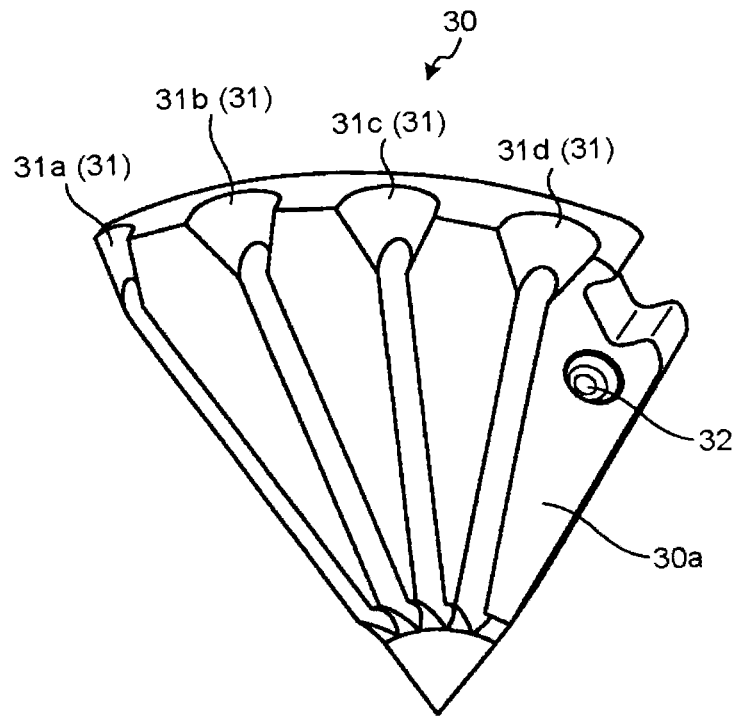
FIG. 4A is a perspective view of a guide part viewed from the probe body side according to the first embodiment.
Figure 4B:
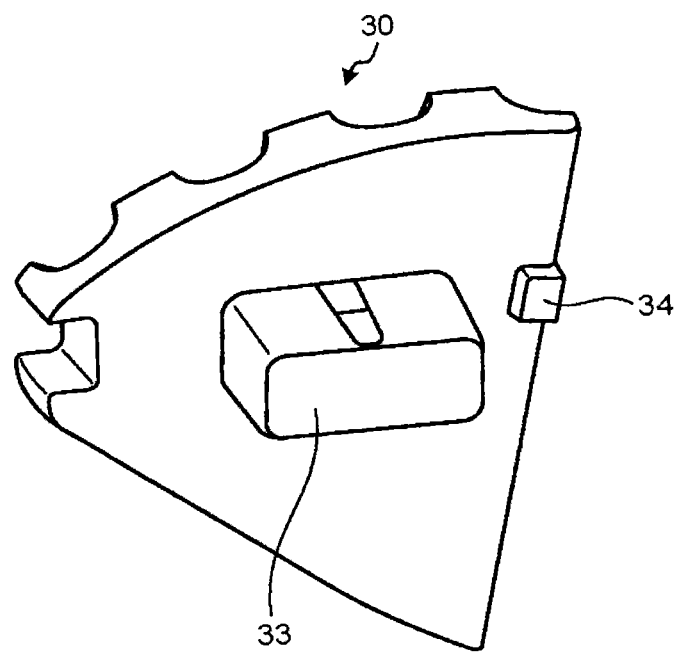
FIG. 4B is a perspective view of the guide part viewed from the adapter side according to the first embodiment.
Figure 4C:
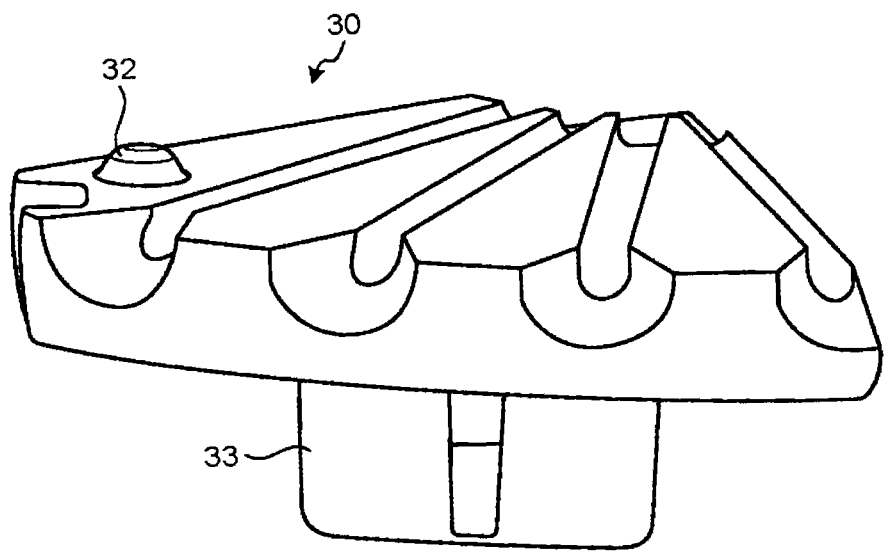
FIG. 4C is a perspective view of the guide part viewed from the gripper side according to the first embodiment.
Figure 4D:
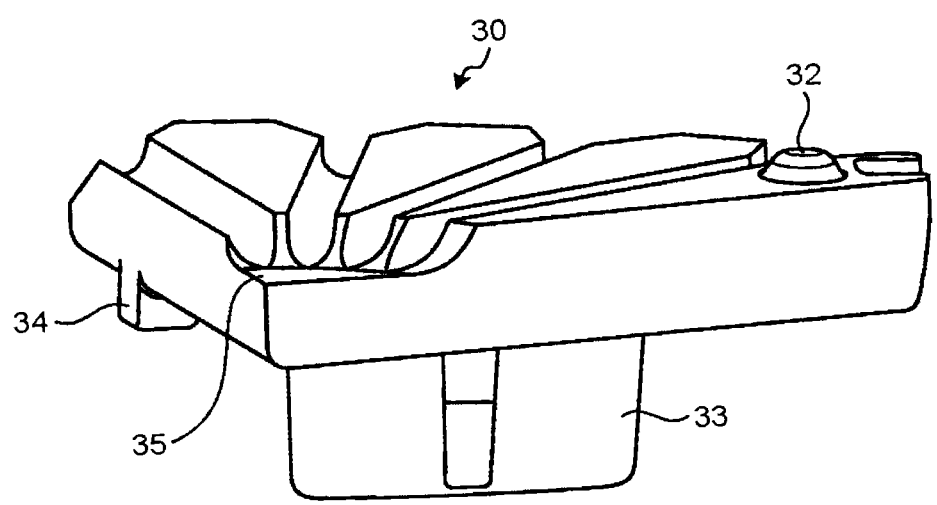
FIG. 4D is a perspective view of the guide part viewed from the probe surface side according to the first embodiment.

The following describes the structure of the guide part 30 with reference to FIGS. 4A to 4D. FIG. 4A is a perspective view of the guide part 30 viewed from the probe body 10 side according to the first embodiment. FIG. 4B is a perspective view of the guide part 30 viewed from the adapter 20 side according to the first embodiment. FIG. 4C is a perspective view of the guide part 30 viewed from the gripper 12 side according to the first embodiment. FIG. 4D is a perspective view of the guide part 30 viewed from the probe surface 14 side according to the first embodiment.

Guide grooves 31 that guide a puncture needle are formed on one surface of the guide part 30. As illustrated in FIG. 4A, for example, the guide part 30 has a plurality of guide grooves 31a, 31b, 31c, and 31d on a surface (also referred to as a third surface) 30a on the probe body side. Because the guide grooves are formed at respective positions and in respective directions, it is possible to perform a puncture on a wider area on an ultrasound image. The surface of the guide part 30 on which the guide grooves 31 are formed is referred to as a "guide groove surface". In the following description, the guide grooves 31a to 31d are collectively referred to as guide grooves 31 unless otherwise distinguished. The number of guide grooves 31 formed on the guide part 30 is not limited to the number illustrated in FIG. 4A.

The guide part 30 has the protrusion 32 at a part with no guide groove formed on the guide groove surface. The protrusion 32 fits into the recess 18 on the first surface 16 of the cutout portion 15. This structure enables the guide part 30 to be positioned at a predetermined position in the cutout portion 15.

As illustrated in FIG. 4B, the guide part 30 has a protrusion 33 and a protrusion 34 on the surface opposite to the guide groove surface.

As illustrated in FIGS. 4C and 4D, the guide groove surface of the guide part 30 are formed into a fan-shape having its apex on the probe surface 14 side and the probe body 10 side. The apex is cut out to form a needle outlet 35 for the puncture needle. In the example illustrated in FIGS. 4C and 4D, four guide grooves are formed at regular intervals on the guide groove surface.

Figure 5:
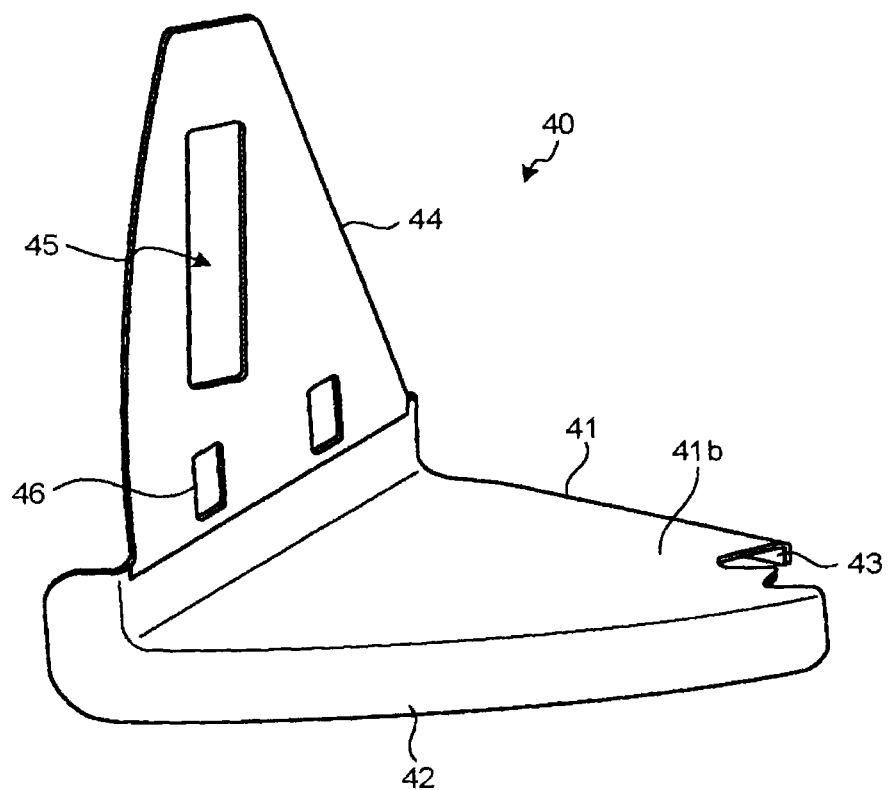
FIG. 5 is a perspective view of a pressing part viewed from the adapter side according to the first embodiment.

The following describes the structure of the pressing part 40 with reference to FIG. 5. FIG. 5 is a perspective view of the pressing part 40 viewed from the adapter 20 side according to the first embodiment. The pressing part 40 is a thin plate and is arranged between the surface of the cutout portion 15 of the probe body 10 and the third surface 30a of the guide part 30 on which the guide grooves 31 are formed. As illustrated in FIG. 5, for example, the pressing part 40 includes a guide part 41 (also referred to as a first thin plate part) and a falling prevention part 44 (also referred to as a second thin plate part). The respective ends of the guide part 41 and the falling prevention part 44 of the pressing part 40 are coupled nearly orthogonally.

As illustrated in FIG. 5, the guide part 41 of the pressing part 40 has a first surface 41a (not illustrated in FIG. 5) and a second surface 41b serving as the back surface of the first surface 41a. In the guide part 41, the first surface 41a corresponds to the surface on the adapter 20 side, whereas the second surface 41b corresponds to the surface on the probe body 10 side. The guide part 41 of the pressing part 40 includes a flange part that covers an edge of the cutout portion 15 of the probe body 10 when being fixed by the fixing part 50 on at least one of the end on the puncture needle inlet side and the end on the puncture needle outlet side. In the example illustrated in FIG. 5, the guide part 41 of the pressing part 40 includes a flange part 42 and a flange part 43. The flange part 42 and the flange part 43 prevent the probe cover from being damaged by the puncture needle.

The falling prevention part 44 of the pressing part 40 has a through hole 45 and a through hole 46. The protrusion 33 of the guide part 30 penetrates into the through hole 45, whereas the protrusion 34 of the guide part 30 penetrates into the through hole 46. In other words, the falling prevention part 44 is sandwiched and fixed between the guide part 30 and the fixing part 50. The through hole 45 and the through hole 46 are effectively used to position the pressing part 40 and to prevent falling of the pressing part 40.

The pressing part 40 preferably has an average thickness of 0.1 to 0.4 mm and an average of the thickness distribution range of equal to or smaller than ±10%. The minimum thickness of the guide part 41 of the pressing part 40 is preferably 0.1 to 0.4 mm, and the maximum thickness of the flange part 42 and the flange part 43 is preferably equal to or larger than 1.5 times the minimum thickness of the guide part 41. The material of the pressing part 40 is preferably a thermoplastic resin having a tensile modulus of elasticity (Young's modulus) of 1 to 4 GPa.

The falling prevention part 44 is flexibly connected to the end of the guide part 41. The pressing part 40 needs to be thin as much as possible, and the thickness of the bent portion is preferably 0.1 to 0.4 mm. To prevent damage when being bent, the pressing part 40 is preferably made of a resin having a tensile modulus of elasticity (Young's modulus) of equal to or lower than 4 GPa.

As described above, the pressing part 40 needs to be thin and have a certain modulus of elasticity. The pressing part 40 needs to be sterilized when a puncture is performed. Because the pressing part 40 is a thin and flexible component, the pressing part 40 is desired to be sterilized in the manufacturing process and thrown away every time a paracentesis is performed. Thus, the material of the pressing part 40 is a thermoplastic resin capable of being molded by injection molding or blow molding, for example, and is selected from a group of polyethylene, polypropylene, polycarbonate, polyacetal, and polyamide.

Figure 6A:
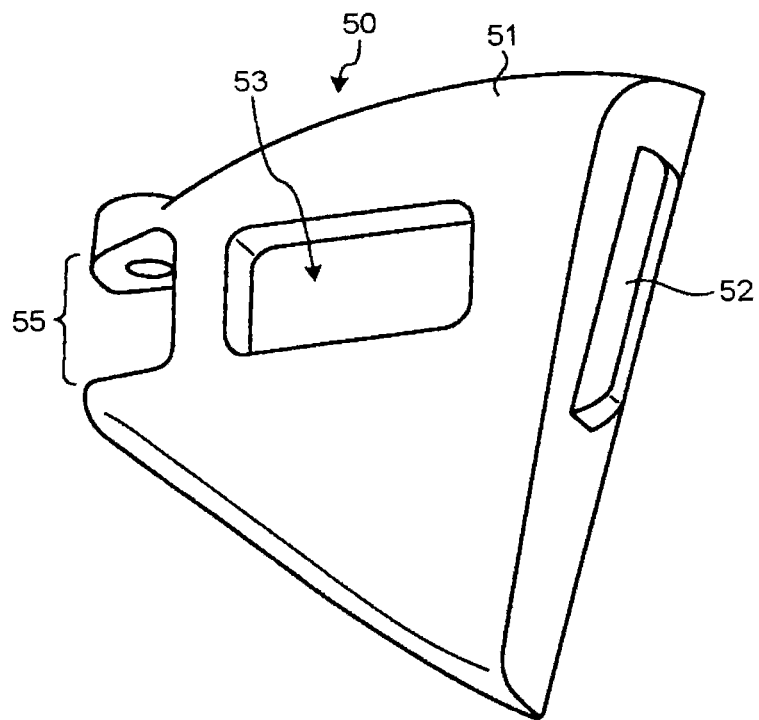
FIG. 6A is a perspective view of a fixing part according to the first embodiment.
Figure 6B:
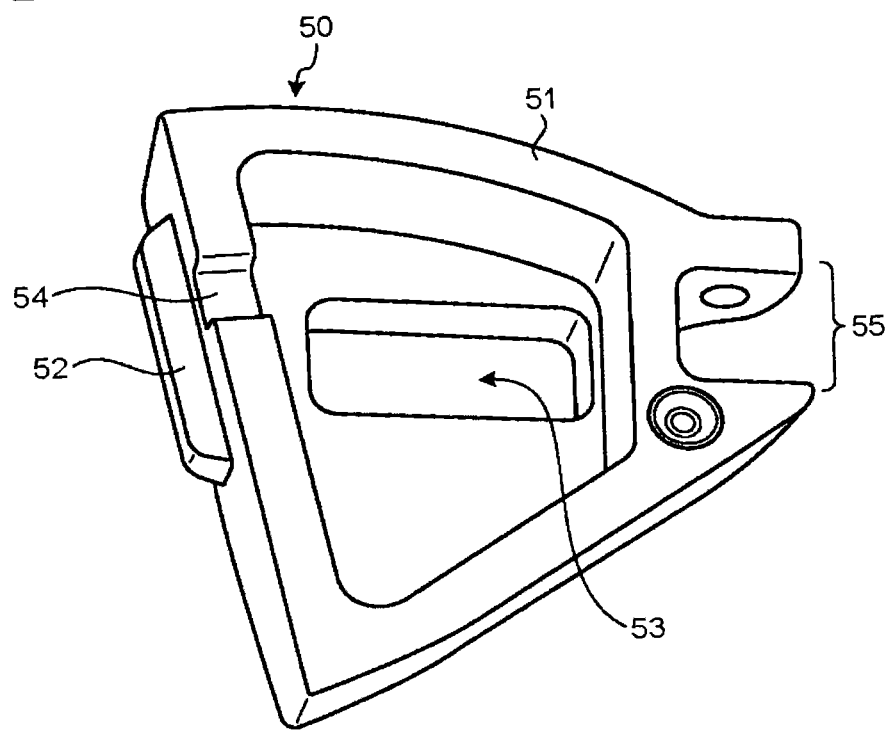
FIG. 6B is another perspective view of the fixing part according to the first embodiment.

The following describes the structure of the fixing part 50 with reference to FIGS. 6A and 6B. FIGS. 6A and 6B are perspective views of the fixing part 50 according to the first embodiment. When the probe body 10 is covered with the cover, the fixing part 50 fixes the guide part 30 and the pressing part 40 to the probe body 10 with the cover interposed between the cutout surface of the cutout portion 15 and the first surface 41a of the pressing part 40 and with the third surface 30a of the guide part 30 brought into contact with the second surface 41b of the pressing part 40. In other words, when the probe body 10 is covered with the cover, the fixing part 50 fixes the guide part 30 and the pressing part 40 with the guide groove surface of the guide part 30 brought into contact with one surface of the pressing part 40 and with a part of the cover interposed between the other surface of the pressing part 40 and the surface of the cutout portion 15.

The fixing part 50 includes a cover part 51 (also referred to as a holding part) and a clamp part 56. The clamp part 56 is not illustrated in FIGS. 6A and 6B and will be described later with reference to FIGS. 7D to 7H. As illustrated in FIG. 6A, for example, the cover part 51 has, on the surface coming into contact with the second surface 17 of the cutout portion 15, a protrusion 52 that fits into the recess 19 of the cutout portion 15. The cover part 51 has, on the surface coming into contact with the surface opposite to the guide groove surface of the guide part 30, a through hole 53 that fits onto the protrusion 33 of the guide part 30. As illustrated in FIG. 6B, the cover part 51 has, on the surface coming into contact with the surface opposite to the guide groove surface, a recess 54 that fits onto the protrusion 34 of the guide part 30. The through hole 53 of the fixing part 50 fits onto the protrusion 33 of the guide part 30. The recess 54 of the fixing part 50 fits onto the protrusion 34 of the guide part 30.

One end of the clamp part 56 is rotatably attached to the cover part 51, and the other end thereof is fastened to the probe body 10, whereby the clamp part 56 fixes the cover part 51. The clamp part 56, for example, is attached to an attachment portion 55 on the surface of the cover part 51 on the side opposite to the surface provided with the protrusion 52 and is rotatable about the cover part 51. The clamp part 56 is fastened to the first surface 16 of the cutout portion 15 with the guide part 30 and the pressing part 40 sandwiched therebetween. Thus, the clamp part 56 fixes the guide part 30 and the pressing part 40 to the probe body 10.

A process for assembling the parts of the adapter 20 will be described with reference to FIGS. 7A to 7H. The following describes a state where the guide part 30 and the pressing part 40 are assembled with reference to FIGS. 7A to 7C.

Figure 7A:
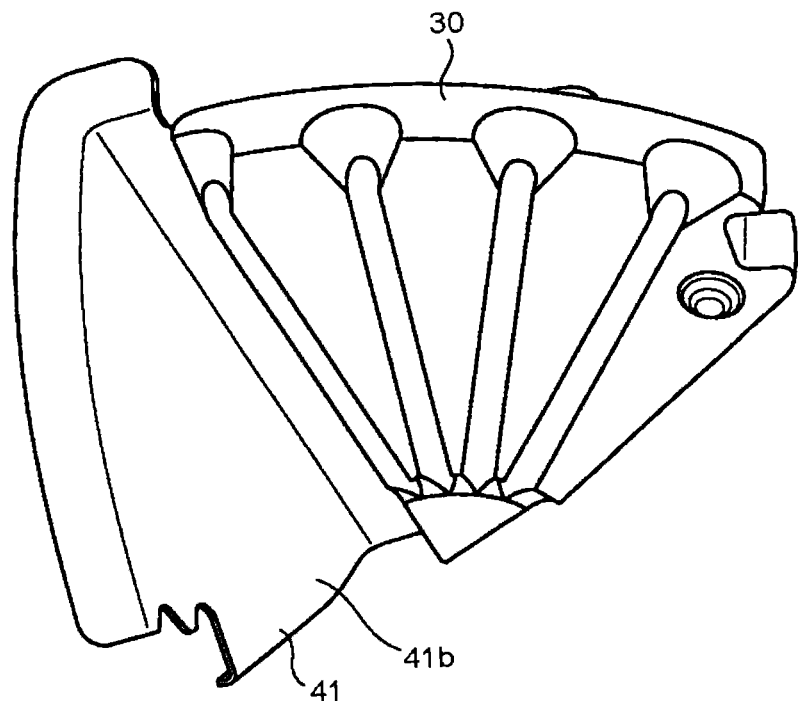
FIG. 7A is a perspective view of the guide part and the pressing part viewed from the probe body side according to the first embodiment.

FIG. 7A is a perspective view of the guide part 30 and the pressing part 40 viewed from the probe body 10 side according to the first embodiment. FIG. 7A illustrates the state where the pressing part 40 is attached to the guide part 30 from the back surface of the guide groove surface. As illustrated in FIG. 7A, the guide part 41 of the pressing part 40 is positioned nearly orthogonally to the guide part 30. The falling prevention part 44 of the pressing part 40 is positioned in a manner overlapping with the guide part 30. In the example illustrated in FIG. 7A, the second surface 41b of the guide part 41 is exposed.

Figure 7B:
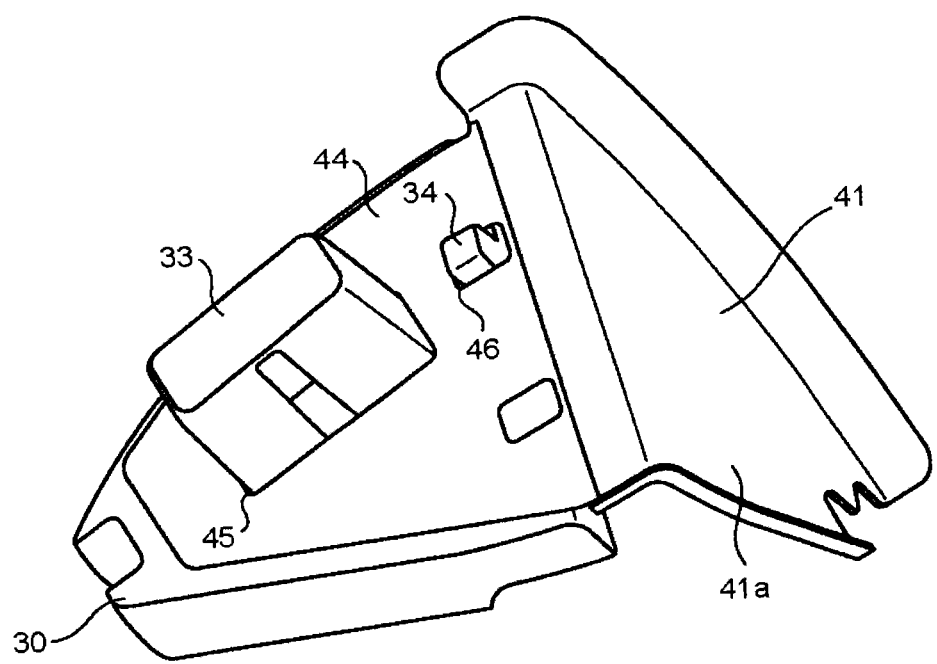
FIG. 7B is a perspective view of the guide part and the pressing part viewed from the adapter side according to the first embodiment.
Figure 7C:
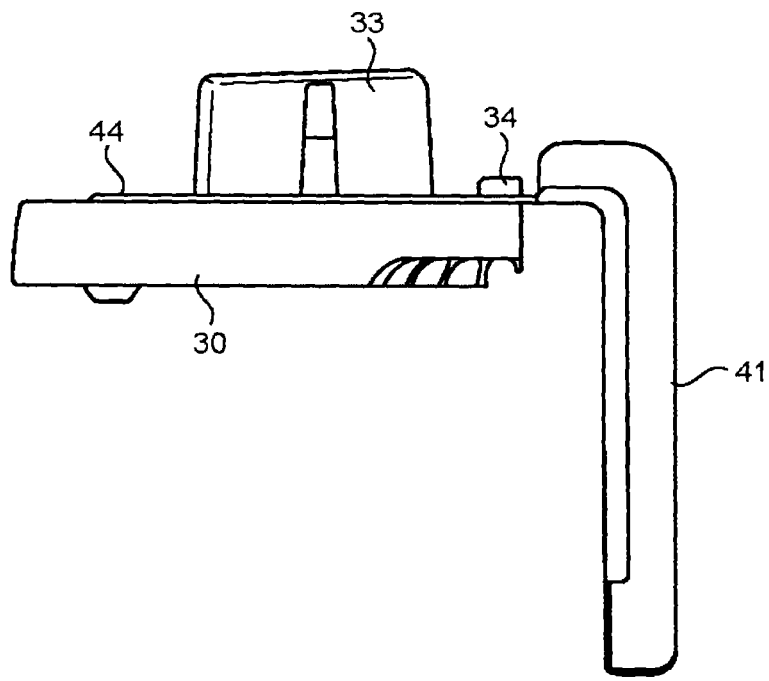
FIG. 7C is a perspective view of the guide part and the pressing part viewed from the probe surface side according to the first embodiment.

FIG. 7B is a perspective view of the guide part 30 and the pressing part 40 viewed from the adapter 20 side according to the first embodiment. FIG. 7C is a perspective view of the guide part 30 and the pressing part 40 viewed from the probe surface 14 side according to the first embodiment. FIGS. 7B and 7C illustrate the position where the guide part 30 engages with the pressing part 40. Specifically, as illustrated in FIG. 7B, the protrusion 33 on the back surface of the guide groove surface of the guide part 30 penetrates into the through hole 45 of the pressing part 40. The protrusion 34 on the back surface of the guide groove surface of the guide part 30 penetrates into the through hole 46 of the pressing part 40. Thus, the guide part 30 and the pressing part 40 are positioned at two points. In the example illustrated in FIG. 7B, the first surface 41a of the guide part 41 is exposed.

Figure 7D:
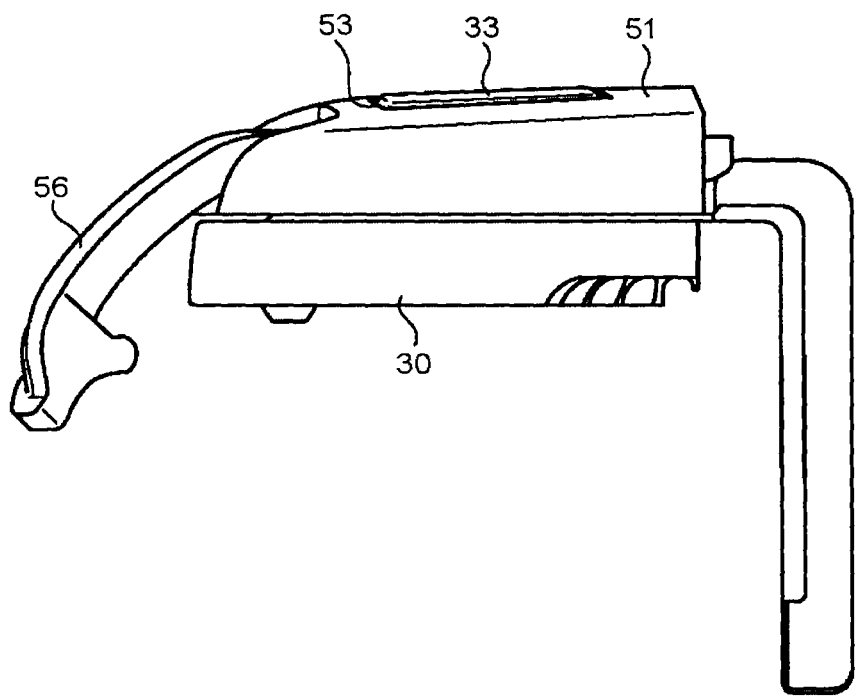
FIG. 7D is a perspective view of the guide part, the pressing part, and the fixing part viewed from the probe surface side according to the first embodiment.
Figure 7E:
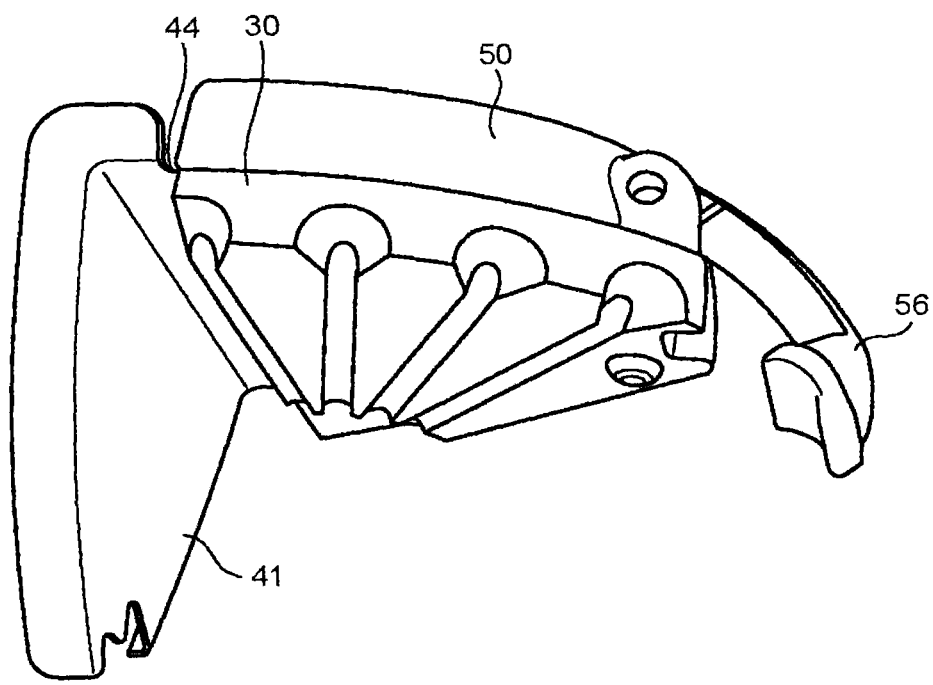
FIG. 7E is a perspective view of the guide part, the pressing part, and the fixing part viewed from the gripper side on the probe body side according to the first embodiment.
Figure 7F:
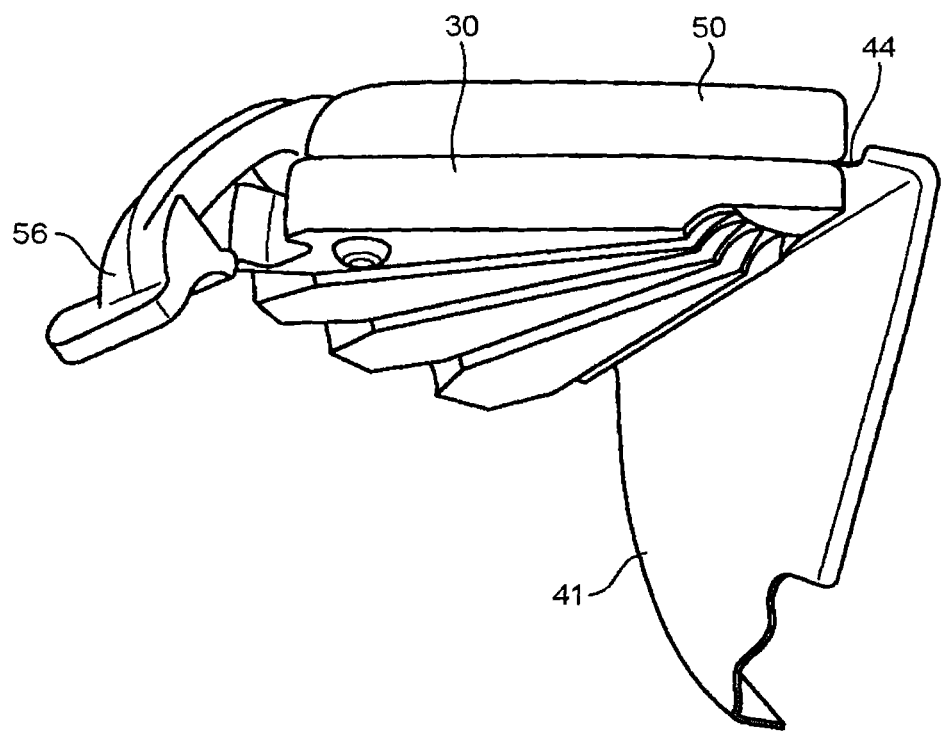
FIG. 7F is a perspective view of the guide part, the pressing part, and the fixing part viewed from the probe surface side on the probe body side according to the first embodiment.

The following describes a state where the guide part 30, the pressing part 40, and the fixing part 50 are assembled with reference to FIGS. 7D to 7F. FIG. 7D is a perspective view of the guide part 30, the pressing part 40, and the fixing part 50 viewed from the probe surface 14 side according to the first embodiment. FIG. 7D illustrates a state where the fixing part 50 is further attached to the structure illustrated in FIG. 7C. The cover part 51 of the fixing part 50 has the through hole 53 that fits onto the protrusion 33 of the guide part 30. The cover part 51 of the fixing part 50 also has the recess 54, which is not illustrated in FIG. 7D, that fits onto the protrusion 34 of the guide part 30. The cover part 51 of the fixing part 50 is provided with the clamp part 56.

FIG. 7E is a perspective view of the guide part 30, the pressing part 40, and the fixing part 50 viewed from the gripper 12 side on the probe body 10 side according to the first embodiment. FIG. 7E illustrates a state where the pressing part 40 is attached to the guide part 30 from the back surface of the guide groove surface, and the fixing part 50 is further attached thereto. As illustrated in FIG. 7E, the falling prevention part 44 of the pressing part 40 is sandwiched and fixed between the guide part 30 and the cover part 51 of the fixing part 50. Specifically, the falling prevention part 44 is arranged between the guide part 30 and the fixing part 50 with the protrusion 33 of the guide part 30 penetrating into the through hole 45 and with the protrusion 34 of the guide part 30 penetrating into the through hole 46. This arrangement can prevent the pressing part 40 from falling off. The guide part 41 of the pressing part 40 is positioned nearly orthogonally to the guide part 30.

FIG. 7F is a perspective view of the guide part 30, the pressing part 40, and the fixing part 50 viewed from the probe surface 14 side on the probe body 10 side according to the first embodiment. Similarly to FIG. 7E, the falling prevention part 44 is arranged between the guide part 30 and the fixing part 50 with the protrusion 33 of the guide part 30 penetrating into the through hole 45 and with the protrusion 34 of the guide part 30 penetrating into the through hole 46 in FIG. 7F.

Figure 7G:
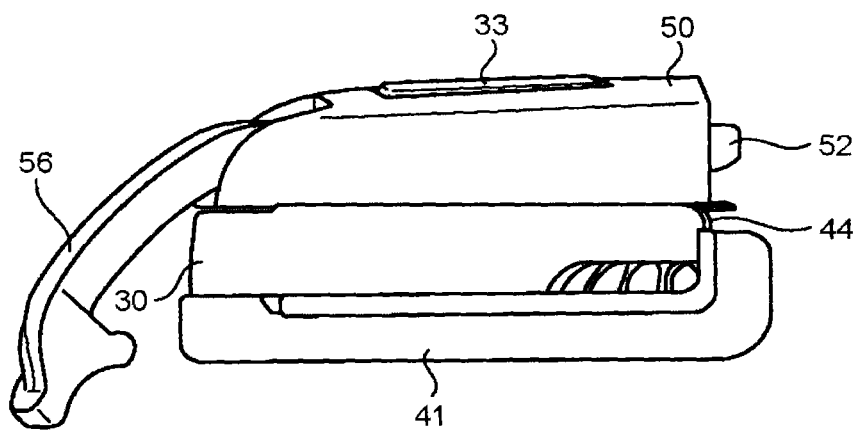
FIG. 7G is a perspective view of the adapter assembled in a manner attachable to the cutout portion according to the first embodiment.
Figure 7H:
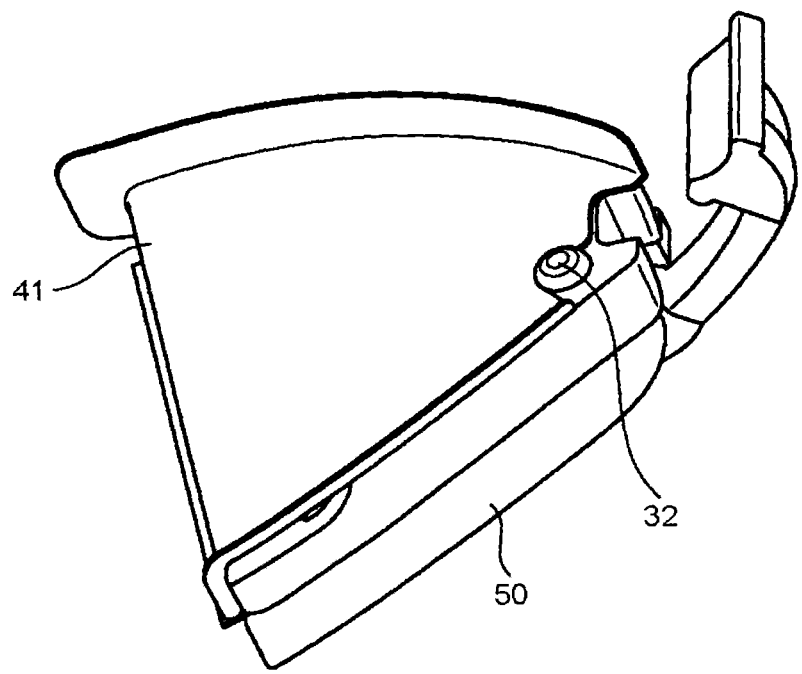
FIG. 7H is another perspective view of the adapter assembled in a manner attachable to the cutout portion according to the first embodiment.

The following describes the adapter 20 assembled in a manner attachable to the cutout portion 15 with reference to FIGS. 7G and 7H. FIGS. 7G and 7H are perspective views of the adapter 20 assembled in a manner attachable to the cutout portion 15 according to the first embodiment.

As illustrated in FIG. 7G, the falling prevention part 44 of the pressing part 40 is bent at the end of the guide part 41. When the adapter 20 is attached to the cutout portion 15 of the ultrasound probe 1 provided with the probe cover, the protrusion 52 of the fixing part 50 fits into the recess 19 of the cutout portion 15. As illustrated in FIG. 7H, the protrusion 32 of the guide part 30 fits into the recess 18 of the cutout portion 15. Thus, the cutout portion 15 and the adapter 20 are positioned in attachment of the adapter 20.

Subsequently, the clamp part 56 rotatably attached to the fixing part 50 is rotated to sandwich the probe. Thus, the guide part 41 is arranged between the surface of the cutout portion 15 and the guide groove surface of the guide part 30 on which the guide grooves 31 are formed. When the probe body 10 is covered with the cover, the cover part 51 holds the guide part 30 and the pressing part 40 with the cover interposed between the cutout surface of the cutout portion 15 and the first surface 41a of the pressing part 40 and with the third surface 30a of the guide part 30 brought into contact with the second surface 41b of the pressing part 40. Thus, the adapter 20 is fixed to the cutout portion 15 of the probe body 10 in the ultrasound probe 1.

As described above, an L-shaped cutout is formed at an end of the probe surface 14 in the first embodiment, and the cutout portion 15 has two surfaces formed along the L-shaped cutout as the cutout surfaces. Thus, the first embodiment can easily attach the adapter 20 onto the probe cover without forming any wrinkle.

The pressing part 40 according to the first embodiment is a thin plate and is arranged between the surface of the cutout portion 15 of the probe body 10 and the third surface 30a of the guide part 30 on which the guide grooves 31 are formed. Thus, the first embodiment can prevent the probe cover from being damaged by the puncture needle at a part sandwiched between the probe body 10 and the guide part 30. The guide part 41 of the pressing part 40 according to the first embodiment has the flange part 42 and the flange part 43. Thus, the first embodiment can prevent the probe cover from being damaged by the puncture needle at the end on the puncture needle inlet side and on the puncture needle outlet side.

The material of the pressing part 40 is selected from a group of polyethylene, polypropylene, polycarbonate, polyacetal, and polyamide, for example. Thus, the pressing part 40 is thin, has a certain modulus of elasticity, and can be manufactured at low cost, for example. By making the pressing part 40 thin, for example, the first embodiment can minimize an influence on the ultrasound effective area in a case where the probe cover is securely fixed to the probe. As a result, the ultrasound probe 1 according to the first embodiment can prevent deterioration of the image quality.

The pressing part 40 according to the first embodiment has a certain modulus of elasticity, for example. To remove the probe with the puncture needle left in a subject body for treatment or the like after insertion of the puncture needle is completed, the first embodiment can smoothly release the puncture needle. Specifically, to remove the probe with the puncture needle left in the subject body for treatment or the like after insertion of the puncture needle is completed, the clamp part 56 is rotated in a direction opposite to that in the attachment. Thus, the adapter 20 is removed from the probe body 10 with the fixing part 50 held. In a case where the falling prevention part 44 of the pressing part 40 is a resin having a tensile modulus of elasticity (Young's modulus) of equal to or lower than 1 GPa, the falling prevention part 44 bent at 90 degrees is opened by an internal repulsive force. In other words, the puncture needle can be smoothly released.

Because the pressing part 40 according to the first embodiment can be manufactured at low cost, for example, the pressing part 40 can be thrown away every time a paracentesis is performed. This can reduce the time for sterilization, thereby improving the throughput of an examination. Specifically, because the adapter 20 is present outside the probe cover, the adapter 20 needs to be sterilized when a paracentesis is performed. Such a product is typically provided in a manner sterilized in the manufacturing process and used only once. The adapter 20 may be sterilized and used only once as a whole. Because the adapter 20 has a plurality of components, however, a user may sterilize the adapter 20 before use, thereby using it more than once. In this case, the guide part 30 and the fixing part 50, for example, are repeatedly sterilized and used every time a paracentesis is performed. In this case, the pressing part 40 is thrown away every time a paracentesis is performed because the pressing part 40 is a thin and flexible component and can be provided at low cost.

Second Embodiment

The ultrasound probe 1 according to a second embodiment will be described. The ultrasound probe 1 according to the second embodiment has the same configuration as that of the ultrasound probe according to the first embodiment except that the configuration of an adapter 60 is different from that of the adapter 20. The second embodiment will describe the configuration of the adapter 60. The adapter 60 fits into the cutout portion 15 of the probe body 10. In other words, the adapter 60 is detachably attached to the cutout portion 15 of the probe body 10.

Figure 8A:
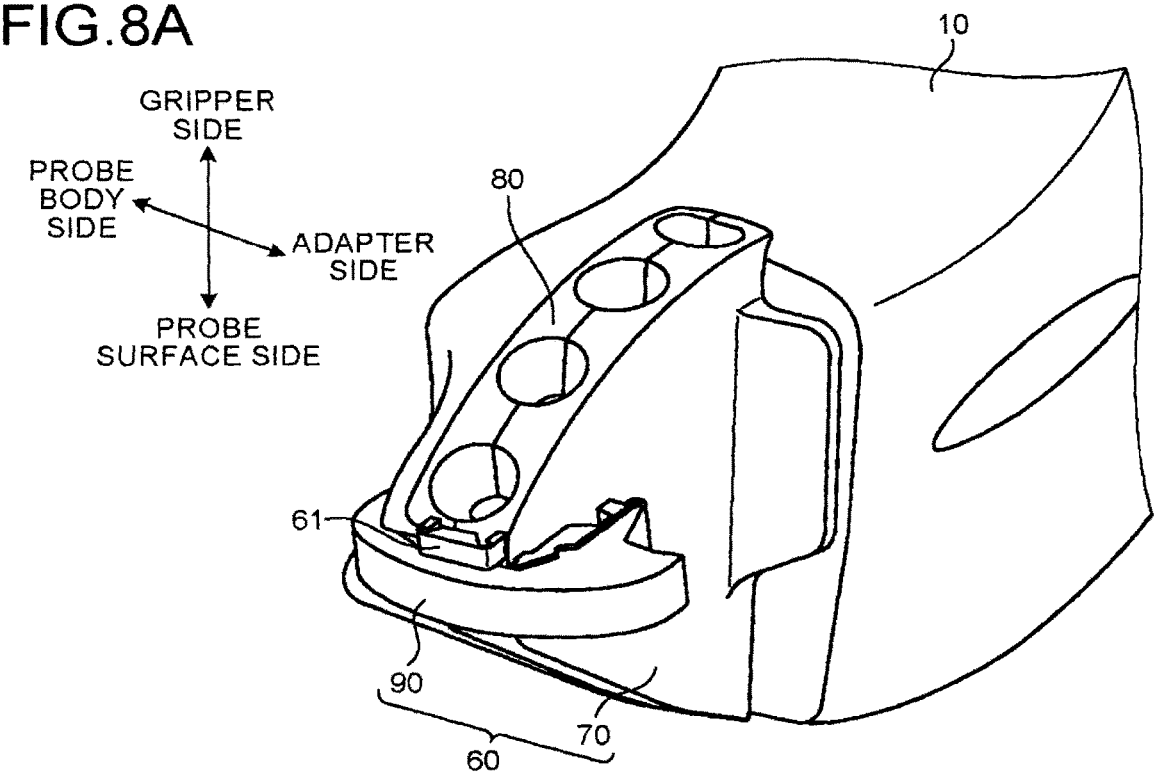
FIG. 8A is a perspective view of a configuration of an adapter according to a second embodiment.
Figure 8B:
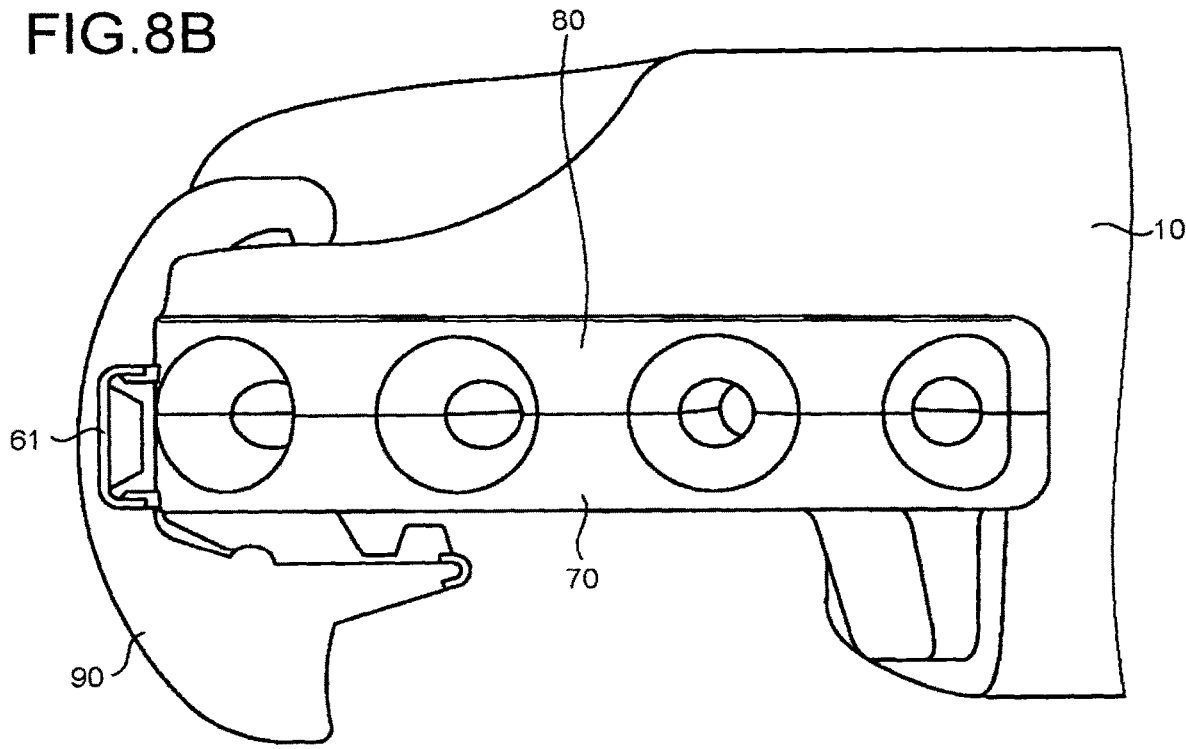
FIG. 8B is another perspective view of the configuration of the adapter according to the second embodiment.

The following describes the configuration of the adapter 60 with reference to FIGS. 8A and 8B. FIGS. 8A and 8B are perspective views of the configuration of the adapter 60 according to the second embodiment. As illustrated in FIG. 8A, the adapter 60 includes a guide part 70 (also referred to as a second pressing part), a pressing part 80 (also referred to as a first pressing part), and a fixing part 90.

The guide part 70 and the pressing part 80 are coupled with a coupling part 61 and thus integrally formed. When the coupling part 61 is bent, the guide part 70 and the pressing part 80 overlap with each other. The coupling part 61 has a hinge structure, for example. The guide part 70 and the pressing part 80 will be described later in detail.

When the probe body 10 is covered with the cover, the fixing part 90 fixes the guide part 70 and the pressing part 80 with the surface of the guide part 70 on which guide grooves are formed brought into contact with one surface of the pressing part 80 and with a part of the cover interposed between the other surface of the pressing part 80 and the surface of the cutout portion 15. The fixing part 90 will be described later in detail.

Figure 9A:
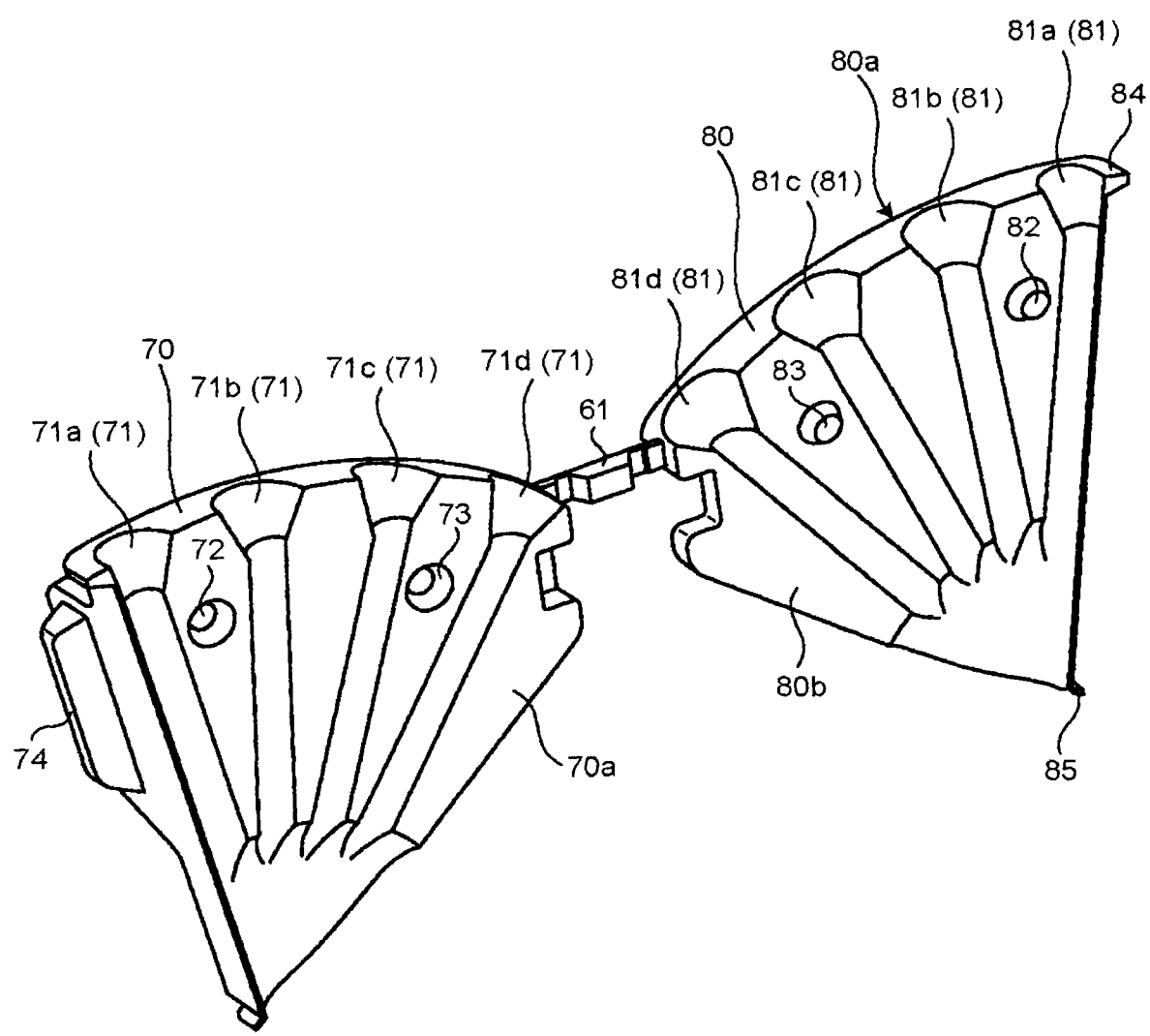
FIG. 9A is a perspective view of a guide part and a pressing part according to the second embodiment.

The following describes the structure of the guide part 70 and the pressing part 80 with reference to FIGS. 9A to 9C. FIGS. 9A to 9C are perspective views of the guide part 70 and the pressing part 80 according to the second embodiment. As illustrated in FIGS. 9A and 9B, the respective ends of the guide part 70 and the pressing part 80 are coupled with the flexible coupling part 61.

As illustrated in FIG. 9A, a plurality of guide grooves 71a, 71b, 71c, and 71d that guide the puncture needle are formed on a surface (also referred to as a third surface) 70a of the guide part 70 coming into contact with one surface of the pressing part 80. Because the guide grooves are formed at respective positions and in respective directions, it is possible to perform a puncture on a wider area on an ultrasound image. The surface of the guide part 70 on which the guide grooves 71 are formed is referred to as a "guide groove surface". In the following description, the guide grooves 71a to 71d are collectively referred to as guide grooves 71 unless otherwise distinguished. The number of guide grooves formed on the guide part 70 is not limited to the number illustrated in FIG. 9A.

The guide part 70 has a recess 72 and a recess 73 at a part with no guide groove formed on the guide groove surface. The recess 72 fits onto a protrusion 82 of the pressing part 80, which will be described later, when the coupling part 61 is bent. The recess 73 fits onto a protrusion 83 of the pressing part 80, which will be described later, when the coupling part 61 is bent. The guide part 70 has a protrusion 74 on the surface coming into contact with the second surface 17 of the cutout portion 15. The protrusion 74 fits into the recess 19 of the cutout portion 15.

The pressing part 80 has a first surface 80a and a second surface 80b serving as the back surface of the first surface 80a. The pressing part 80 is a thin plate and is arranged between the surface of the cutout portion 15 of the probe body 10 and the third surface 70a of the guide part 70 on which the guide grooves are formed. A plurality of guide grooves 81a, 81b, 81c, and 81d are formed on the second surface 80b of the pressing part 80. In the following description, the guide grooves 81a to 81d are collectively referred to as guide grooves 81 unless otherwise distinguished. The guide grooves 81 are formed at positions facing the respective guide grooves 71 of the guide part 70 when the guide groove surface of the guide part 70 comes into contact with the guide groove surface of the pressing part 80.

The pressing part 80 has the protrusion 82 and the protrusion 83 at a part with no guide groove formed on the guide groove surface. The protrusion 82 fits into the recess 72 of the guide part 70 when the coupling part 61 is bent. The protrusion 83 fits into the recess 73 of the guide part 70 when the coupling part 61 is bent.

The pressing part 80 includes, on at least one of the end on the puncture needle inlet side and the end on the puncture needle outlet side, a flange part that covers an edge of the cutout portion 15 of the probe body 10 when the pressing part 80 is fixed by the fixing part 90. In other words, the pressing part 80 includes a flange part spreading from the surface coming into contact with the guide part 70 toward the probe body 10 on at least one of the end on the puncture needle inlet side and the end on the puncture needle outlet side. In the example illustrated in FIG. 9A, the pressing part 80 includes a flange part 84 near the needle inlet of the pressing part 80 and a flange part 85 near the needle outlet of the pressing part 80. With the flange part 84 and the flange part 85, the ultrasound probe 1 can prevent the probe cover from being damaged by the puncture needle.

FIG. 9C is a side view of the guide part 70 and the pressing part 80 viewed from the gripper 12 side according to the second embodiment. As illustrated in FIG. 9C, the coupling part 61 couples an end of the surface of the guide part 70 opposite to the guide groove surface (third surface 70a) to a part of the pressing part 80 near the center of the side surface connecting the first surface 80a and the second surface 80b.

The following describes a process for assembling the guide part 70 and the pressing part 80 with reference to FIGS. 10A to 10E. FIGS. 10A to 10E are perspective views of a state where the guide part 70 and the pressing part 80 are assembled.

Figure 10A:
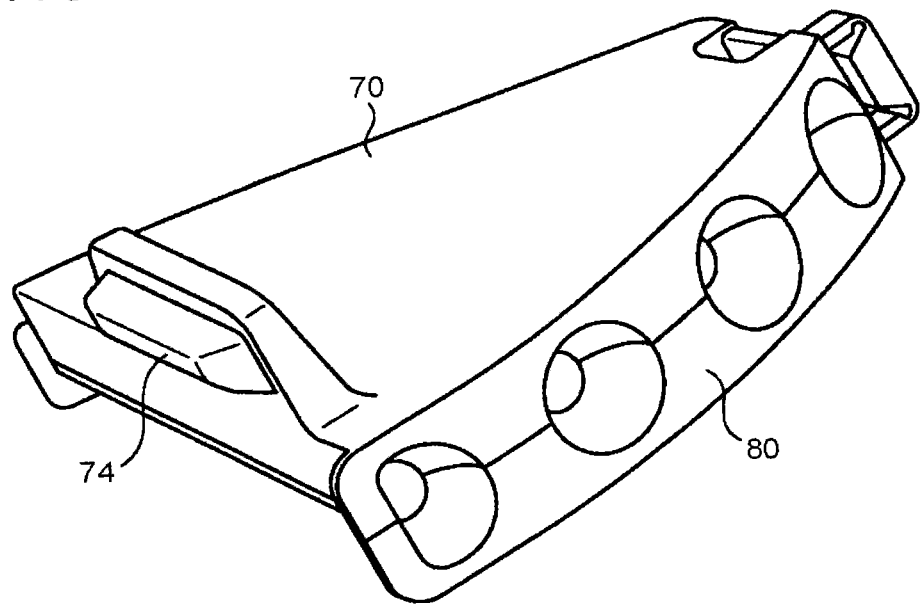
FIG. 10A is a perspective view of the guide part and the pressing part viewed from the gripper side and the adapter side according to the second embodiment.

FIG. 10A is a perspective view of the guide part 70 and the pressing part 80 viewed from the gripper 12 side and the adapter 60 side according to the second embodiment. As illustrated in FIG. 10A, by bending the coupling part 61, the third surface 70a of the guide part 70 comes into contact with the second surface 80b of the pressing part 80. When the coupling part 61 is bent, the guide groove surface of the guide part 70 is tightly attached to the guide groove surface of the pressing part 80. The pairs of guide grooves each form the inlet of the puncture needle.

Figure 10B:
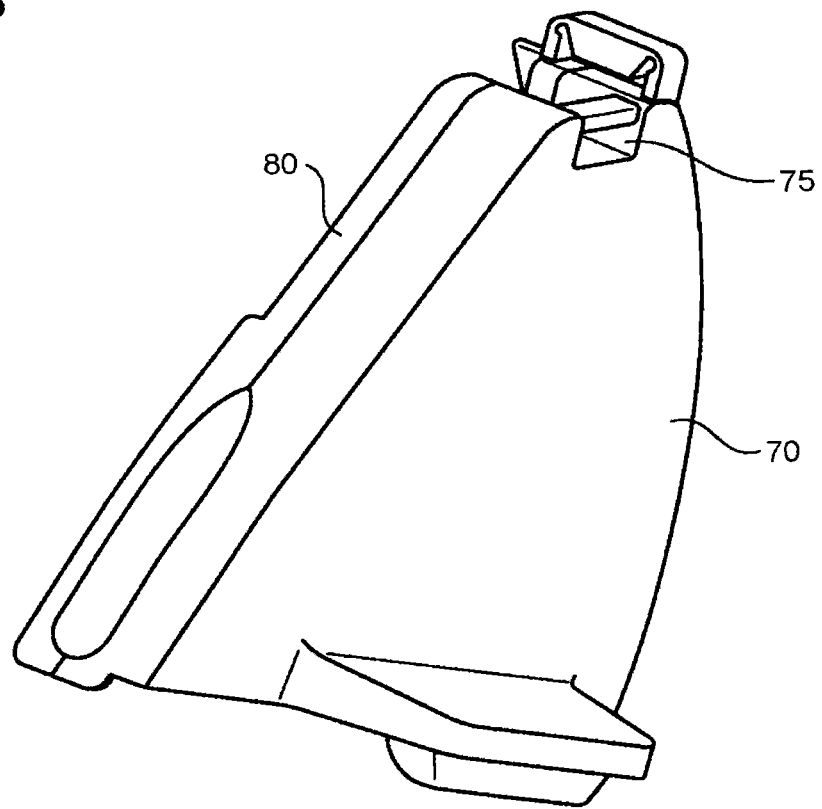
FIG. 10B is a perspective view of the guide part and the pressing part viewed from the probe surface side and the adapter side according to the second embodiment.

FIG. 10B is a perspective view of the guide part 70 and the pressing part 80 viewed from the probe surface 14 side and the adapter 60 side according to the second embodiment. As illustrated in FIG. 10B, when the coupling part 61 is bent, the guide groove surface of the guide part 70 is tightly attached to the guide groove surface of the pressing part 80. The pairs of guide grooves each form the outlet of the puncture needle. The guide part 70 has an attachment portion 75 to which the fixing part 90, which will be described later, is attached.

Figure 10C:
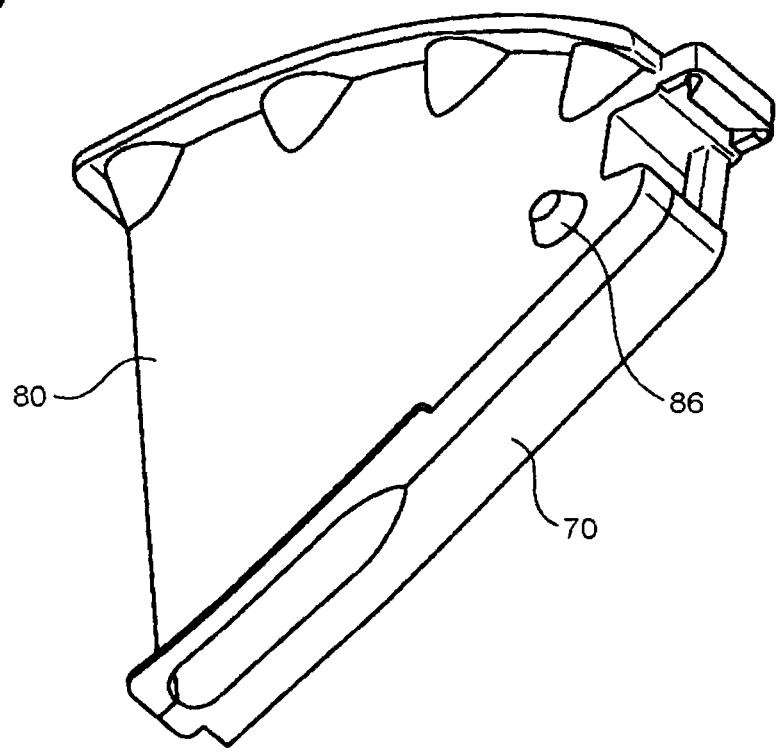
FIG. 10C is a perspective view of the guide part and the pressing part viewed from the probe body side and the probe surface side according to the second embodiment.

FIG. 10C is a perspective view of the guide part 70 and the pressing part 80 viewed from the probe body 10 side and the probe surface 14 side according to the second embodiment. The pressing part 80 has a protrusion 86 on the surface opposite to the guide groove surface. The protrusion 86 fits into the recess 18 on the first surface 16 of the cutout portion 15.

Figure 10D:
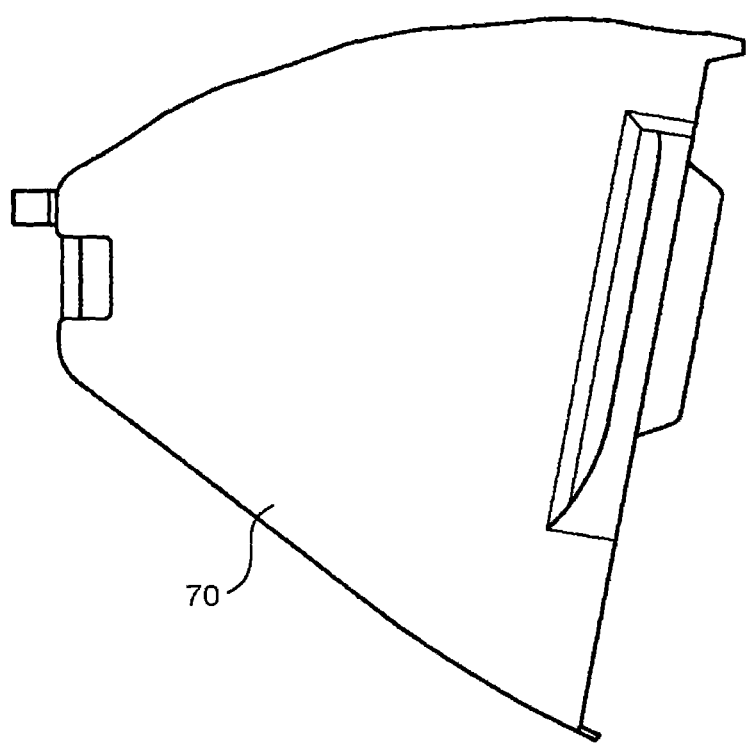
FIG. 10D is a side view of the guide part viewed from the adapter side according to the second embodiment.
Figure 10E:
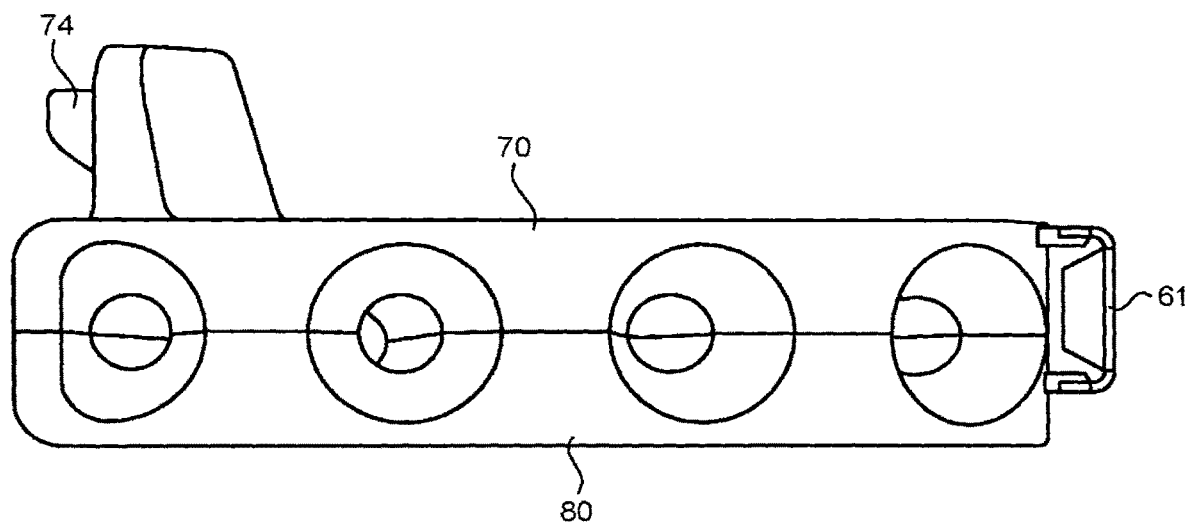
FIG. 10E is a side view of the guide part and the pressing part viewed from the gripper side according to the second embodiment.

FIG. 10D is a side view of the guide part 70 viewed from the adapter 60 side according to the second embodiment. As illustrated in FIG. 10D, the guide part 70 has a planar shape. FIG. 10E is a side view of the guide part 70 and the pressing part 80 viewed from the gripper 12 side according to the second embodiment. As illustrated in FIG. 10E, cylindrical inlets inclined at respective angles are formed.

Figure 11A:
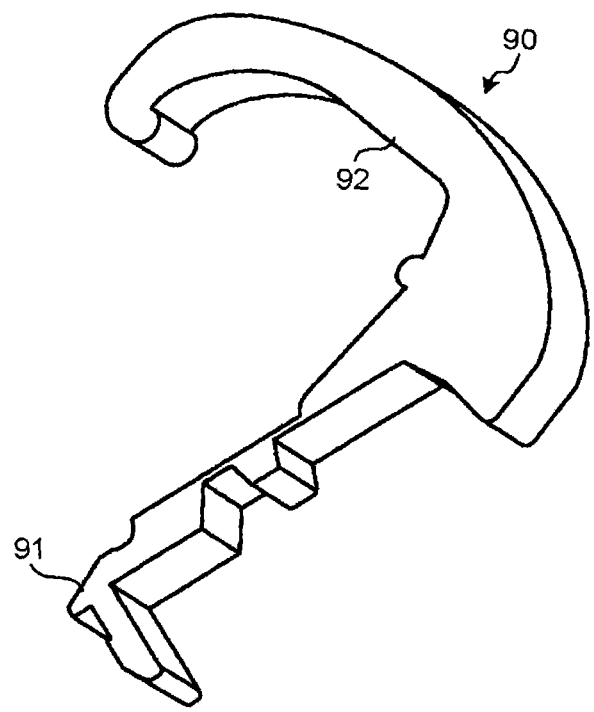
FIG. 11A is a perspective view of a fixing part according to the second embodiment.
Figure 11B:
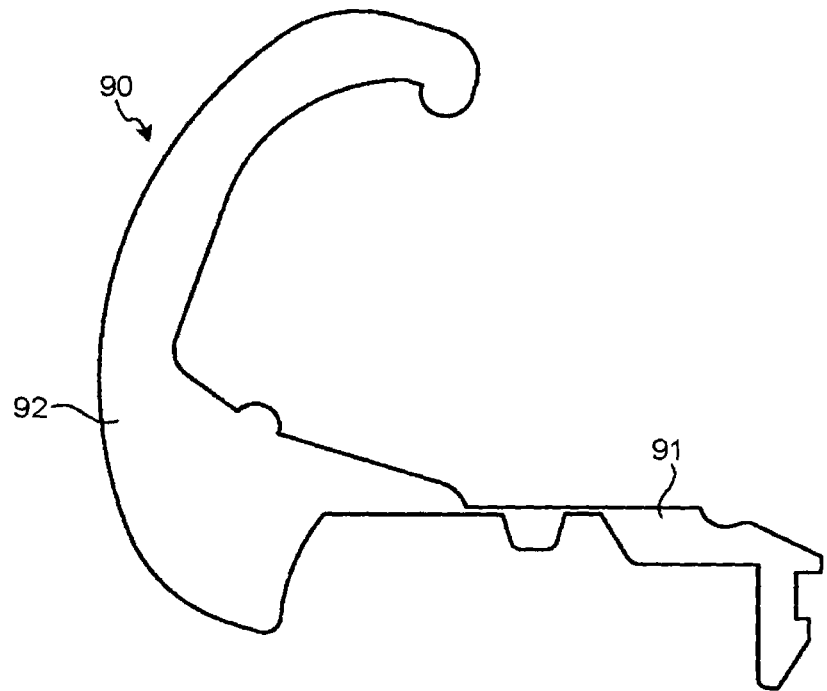
FIG. 11B is another perspective view of the fixing part according to the second embodiment.

The following describes the structure of the fixing part 90 with reference to FIGS. 11A to 11D. FIGS. 11A to 11D are perspective views of the fixing part 90 according to the second embodiment. As illustrated in FIGS. 11A and 11B, the fixing part 90 has a first hinge 91 and a second hinge 92 each of which is foldable. When the probe body 10 is covered with the cover, the fixing part 90 fixes the guide part 70 and the pressing part 80 to the probe body 10 with the cover interposed between the cutout surface of the cutout portion 15 and the first surface 80a of the pressing part 80 and with the third surface 70a of the guide part 70 brought into contact with the second surface 80b of the pressing part 80.

Figure 11C:
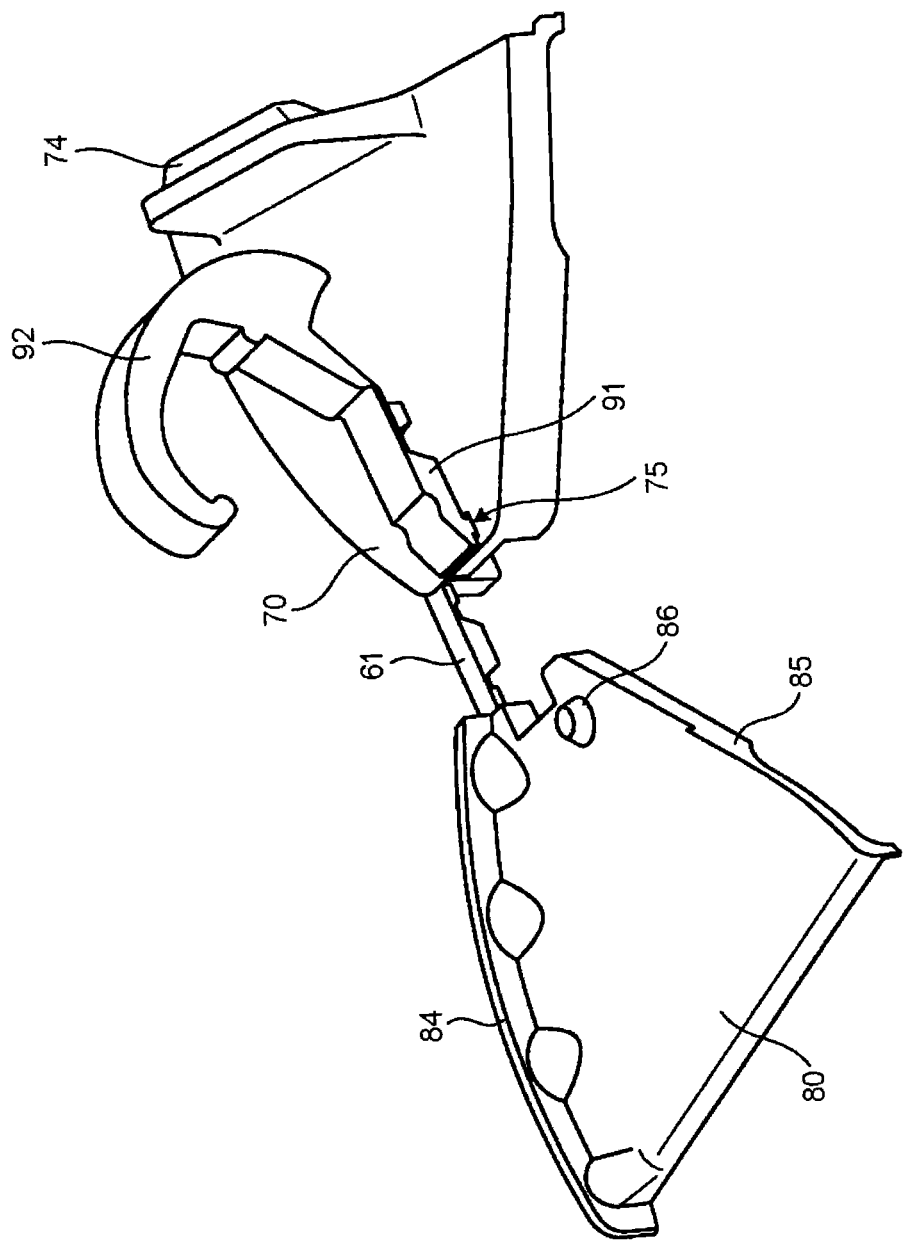
FIG. 11C is still another perspective view of the fixing part according to the second embodiment.

The following describes a state where the fixing part 90 is inserted into the guide part 70 with reference to FIGS. 11C and 11D. FIG. 11C is a perspective view of a state where the fixing part 90 is inserted into the guide part 70 according to the second embodiment. FIG. 11D is another perspective view of a state where the fixing part 90 is inserted into the guide part 70 according to the second embodiment. As illustrated in FIGS. 11C and 11D, a first end of the fixing part 90 is rotatably attached to the guide part 70. The first hinge 91 of the fixing part 90, for example, is inserted into and fixed to the attachment portion 75 of a hinge structure in the guide part 70.

Figure 12A:
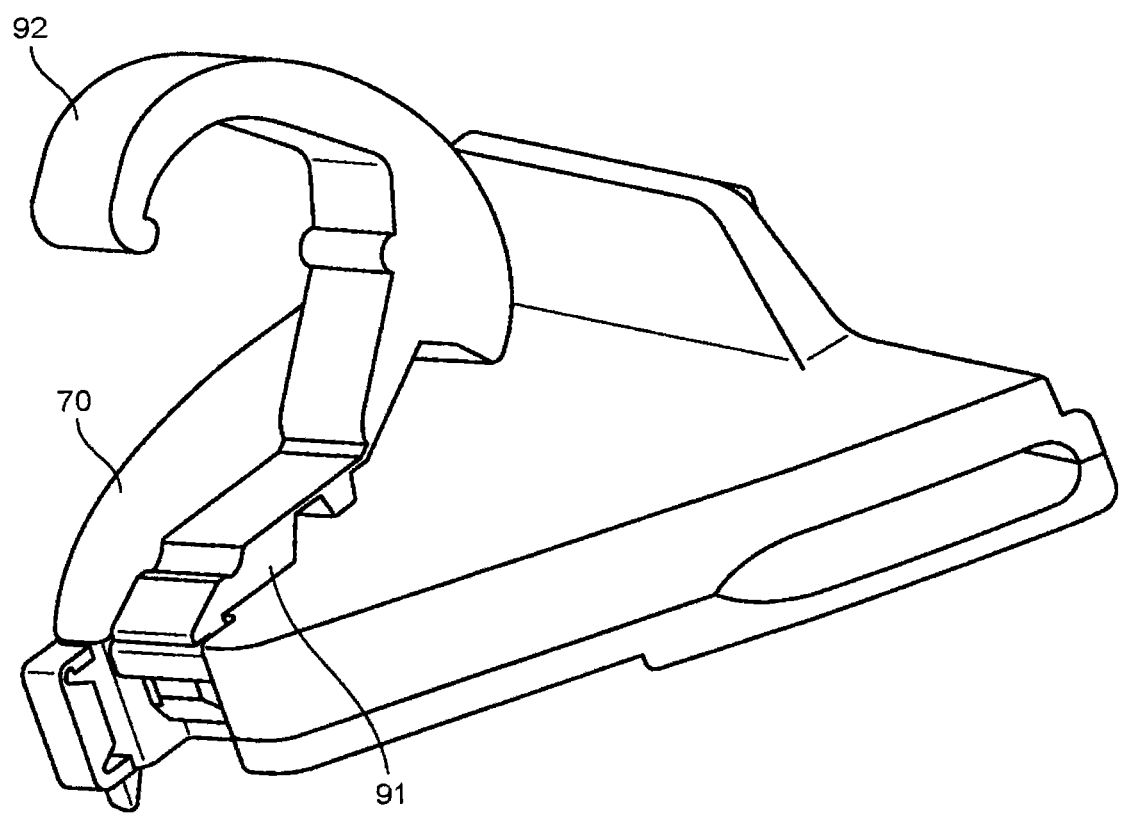
FIG. 12A is a view for explaining a process for attaching the adapter to the cutout portion of the probe body according to the second embodiment.
Figure 12B:
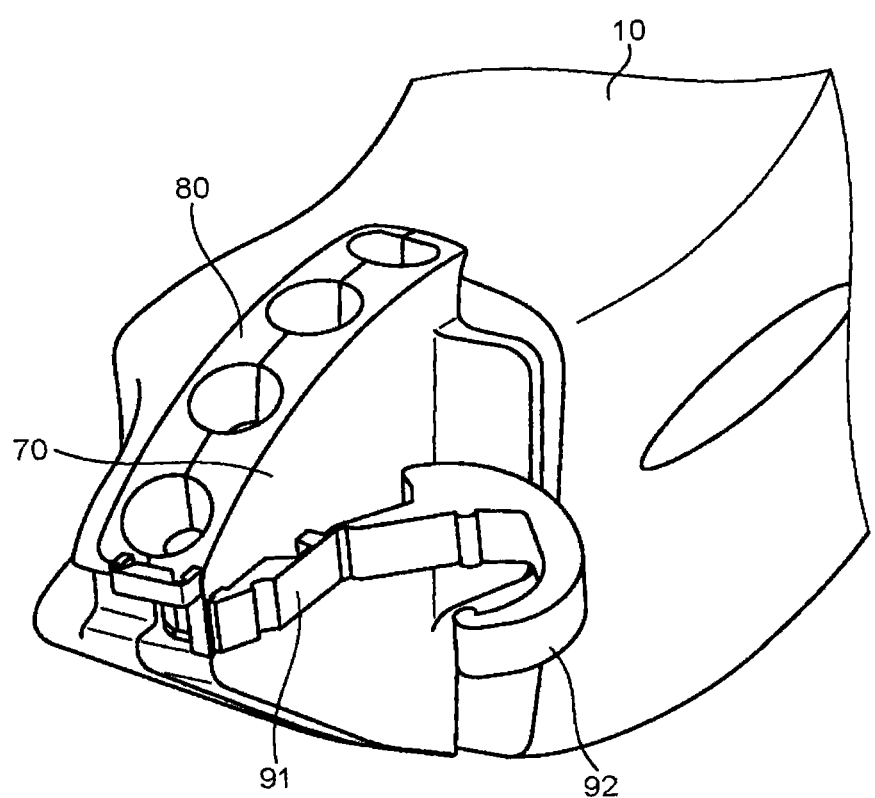
FIG. 12B is another view for explaining the process for attaching the adapter to the cutout portion of the probe body according to the second embodiment.

The following describes a process for attaching the adapter 60 to the cutout portion 15 of the probe body 10 with reference to FIGS. 12A and 12B. FIGS. 12A and 12B are views for explaining a process for attaching the adapter 60 to the cutout portion 15 of the probe body 10 according to the second embodiment. When the adapter 60 is attached to the cutout portion 15, the protrusion 74 of the guide part 70 of the adapter 60 fits into the recess 19 of the cutout portion 15. The protrusion 86 of the pressing part 80 of the adapter 60 fits into the recess 18 of the cutout portion 15. By positioning the adapter 60 and the cutout portion 15 in this manner, the adapter 60 is attached to the cutout portion 15.

Subsequently, as illustrated in FIG. 12B, the second hinge 92 of the fixing part 90 is fastened to the first surface 16 of the cutout portion 15 with the guide part 70 and the pressing part 80 sandwiched therebetween. Thus, the fixing part 90 fixes the guide part 70 and the pressing part 80 to the probe body 10 with the third surface 70a of the guide part 70 brought into contact with the second surface 80b of the pressing part 80. In other words, when the probe body 10 is covered with the cover, a second end of the fixing part 90 is fastened to the probe body 10 with the cover interposed between the cutout surface of the cutout portion 15 and the first surface 80a of the pressing part 80 and with the third surface 70a of the guide part 70 brought into contact with the second surface 80b of the pressing part 80. Thus, the fixing part 90 fixes the guide part 70 and the pressing part 80 to the probe body 10.

As described above, an L-shaped cutout is formed at an end of the probe surface 14 in the second embodiment, and the cutout portion 15 has two surfaces formed along the L-shaped cutout as the cutout surfaces. Thus, the second embodiment can easily attach the adapter 60 onto the probe cover without forming any wrinkles.

The pressing part 80 according to the second embodiment is a thin plate and is arranged between the surface of the cutout portion 15 of the probe body 10 and the third surface 70a of the guide part 70 on which the guide grooves 71 are formed. Thus, the second embodiment can prevent the probe cover from being damaged by the puncture needle at a part sandwiched between the probe body 10 and the guide part 70. The pressing part 80 according to the second embodiment has the flange part 84 and the flange part 85. Thus, the second embodiment can prevent the probe cover from being damaged by the puncture needle at the end on the puncture needle inlet side and on the puncture needle outlet side.

By making the pressing part 80 thin, for example, the second embodiment can minimize an influence on the ultrasound effective area in a case where the probe cover is securely fixed to the probe. As a result, the ultrasound probe 1 according to the second embodiment can prevent deterioration of the image quality.

The guide part 70 and the pressing part 80 according to the second embodiment are coupled with the coupling part 61 and thus integrally formed. With this configuration, the second embodiment requires a smaller number of components of the adapter 60.

In the second embodiment, the third surface 70a of the guide part 70 has the guide grooves 71, and the second surface 80b of the pressing part 80 has the guide grooves 81, for example. The guide grooves that guide the puncture needle may be formed on at least one of the third surface 70*a* of the guide part 70 and the second surface 80*b* of the pressing part 80. The third surface 70*a* of the guide part 70 may have the guide grooves 71, and the second surface 80*b* of the pressing part 80 may have no guide groove, for example. Alternatively, the third surface 70*a* of the guide part 70 may not have the guide grooves 71, and the second surface 80*b* of the pressing part 80 may have the guide grooves 81.

Modification of the Second Embodiment

While the guide part 70 and the pressing part 80 according to the second embodiment are coupled with the coupling part 61 and thus integrally formed, the embodiment is not limited thereto. The guide part 70 and the pressing part 80 may not be coupled with the coupling part 61 and may be individually formed, for example. An adapter 460 according to a modification of the second embodiment, for example, includes a guide part 470 (also referred to as a second pressing part), a pressing part 480 (also referred to as a first pressing part), and a fixing part 490. Similarly to the adapter 60 according to the second embodiment, the adapter 460 according to the modification of the second embodiment fits into the probe body 10. More specifically, the pressing part 480 fits into the recess 18 on the first surface 16 of the cutout portion 15, and the guide part 470 fits into the recess 19 of the cutout portion 15. The parts of the adapter 460 according to the modification of the second embodiment will be described in detail.

Figure 13A:
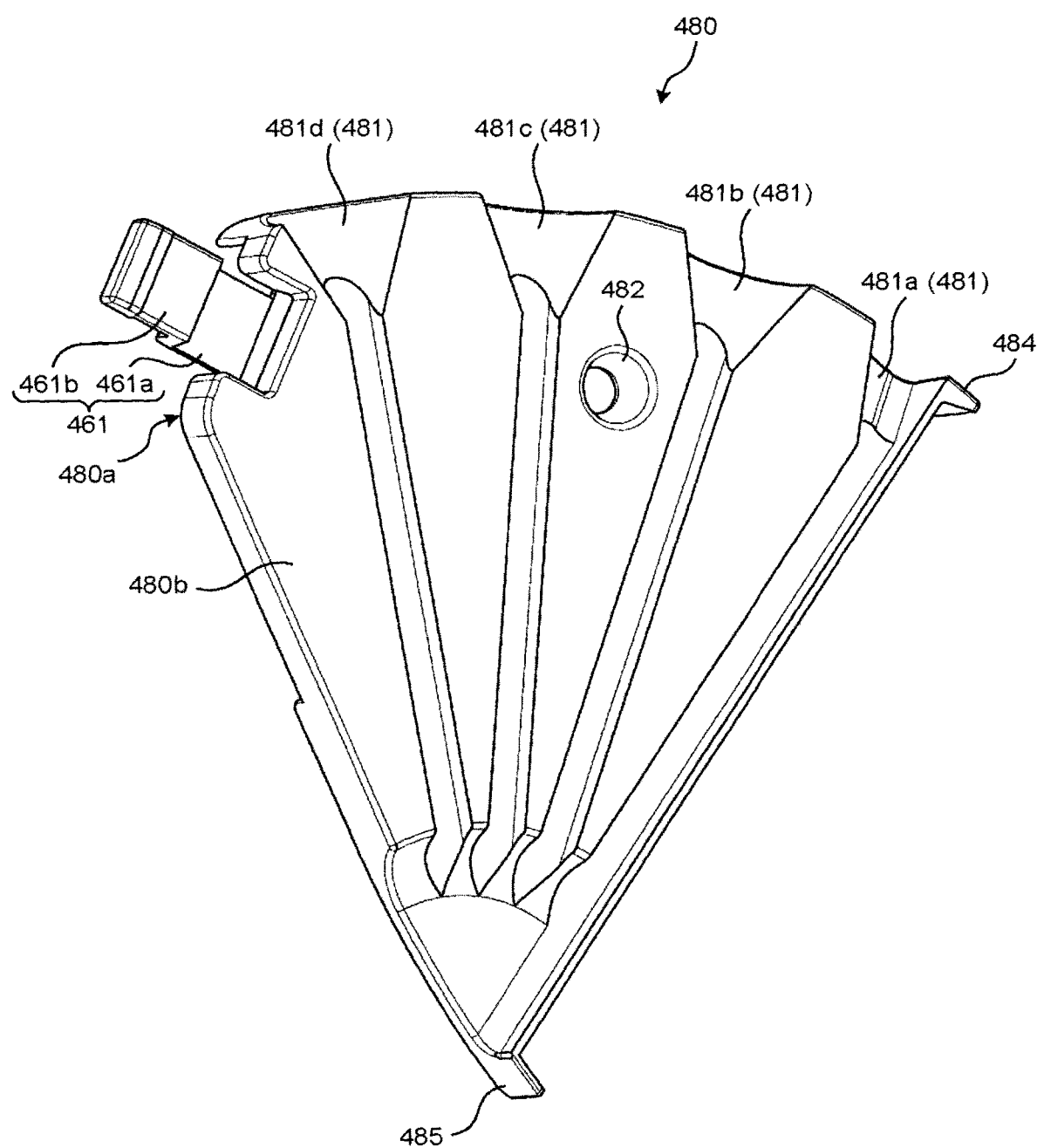
FIG. 13A is a perspective view of a pressing part according to a modification of the second embodiment.
Figure 13B:
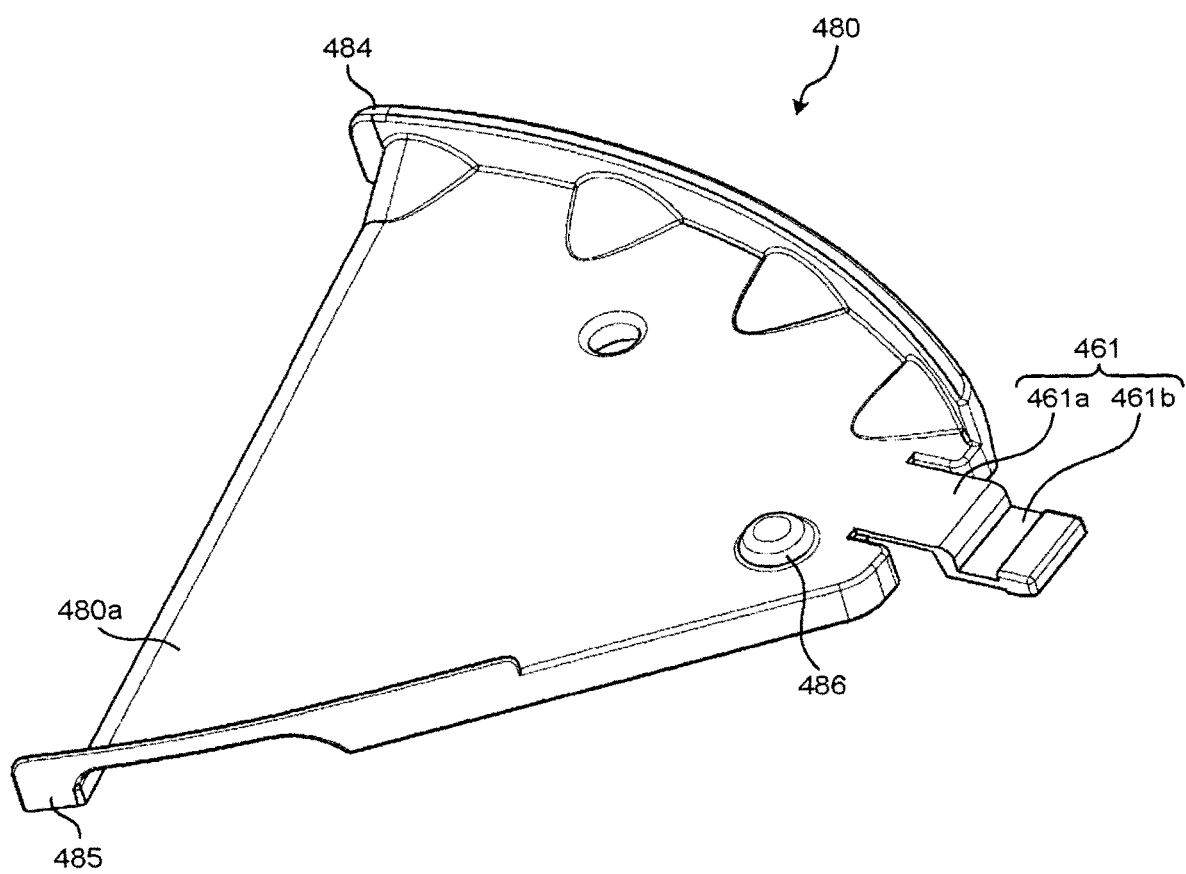
FIG. 13B is another perspective view of the pressing part according to the modification of the second embodiment.

The following describes the structure of the pressing part 480 with reference to FIGS. 13A and 13B. FIGS. 13A and 13B are perspective views of the pressing part 480 according to the modification of the second embodiment. The pressing part 480 is a thin plate and is arranged between the surface of the cutout portion 15 of the probe body 10 and a third surface 470*a* of the guide part 470, which will be described later. As illustrated in FIGS. 13A and 13B, the pressing part 480 has a first surface 480*a* and a second surface 480*b* serving as the back surface of the first surface 480*a*. In other words, the pressing part 480 has the first surface 480*a* and the second surface 480*b* opposite to the first surface 480*a*.

A plurality of guide grooves 481*a*, 481*b*, 481*c*, and 481*d* are formed on the second surface 480*b* of the pressing part 480. Because the guide grooves are formed at respective positions and in respective directions, it is possible to perform a puncture on a wider area on an ultrasound image. In the following description, the guide grooves 481*a* to 481*d* are collectively referred to as guide grooves 481 unless otherwise distinguished. The surface of the pressing part 480 on which the guide grooves 481 are formed is referred to as a "guide groove surface".

The pressing part 480 has a recess 482 at a part with no guide groove formed on the guide groove surface. The recess 482 fits onto a protrusion 472 of the guide part 470. Thus, the guide groove surface of the guide part 470 is tightly attached to the guide groove surface of the pressing part 480. The pairs of guide grooves each form the inlet of the puncture needle.

The pressing part 480 has a flexible connection 461 at an end. The connection 461 has a first area 461*a* and a second area 461*b*. The first area 461*a* is formed at the end on the puncture needle inlet side on the first surface 480*a*. The first area 461*a* can be folded and is integrally formed with the second area 461*b*. The second area 461*b* is inserted into a through hole 475 formed in the guide part 470, which will be described later, and is fixed by engaging with the guide part 470 and the fixing part 490. In other words, the connection 461 connects the respective ends of the guide part 470 and the pressing part 480. The engagement state of the second area 461*b*, the guide part 470, and the fixing part 490 in the through hole 475 will be described later.

The pressing part 480 includes, on at least one of the end on the puncture needle inlet side and the end on the puncture needle outlet side, a flange part that covers an edge of the cutout portion 15 of the probe body 10 when the pressing part 480 is fixed to the probe body 10 by the fixing part 490. In other words, the pressing part 480 includes a flange part spreading from the surface coming into contact with the guide part 470 toward the probe body 10 on at least one of the end on the puncture needle inlet side and the end on the puncture needle outlet side. In the example illustrated in FIGS. 13A and 13B, the pressing part 480 includes a flange part 484 near the needle inlet of the pressing part 480 and a flange part 485 near the needle outlet of the pressing part 480. With the flange part 484 and the flange part 485, the ultrasound probe 1 can prevent the probe cover from being damaged by the puncture needle.

As illustrated in FIG. 13B, the pressing part 480 has a protrusion 486 on the surface opposite to the guide groove surface. The protrusion 486 fits into the recess 18 on the first surface 16 of the cutout portion 15.

Figure 14A:
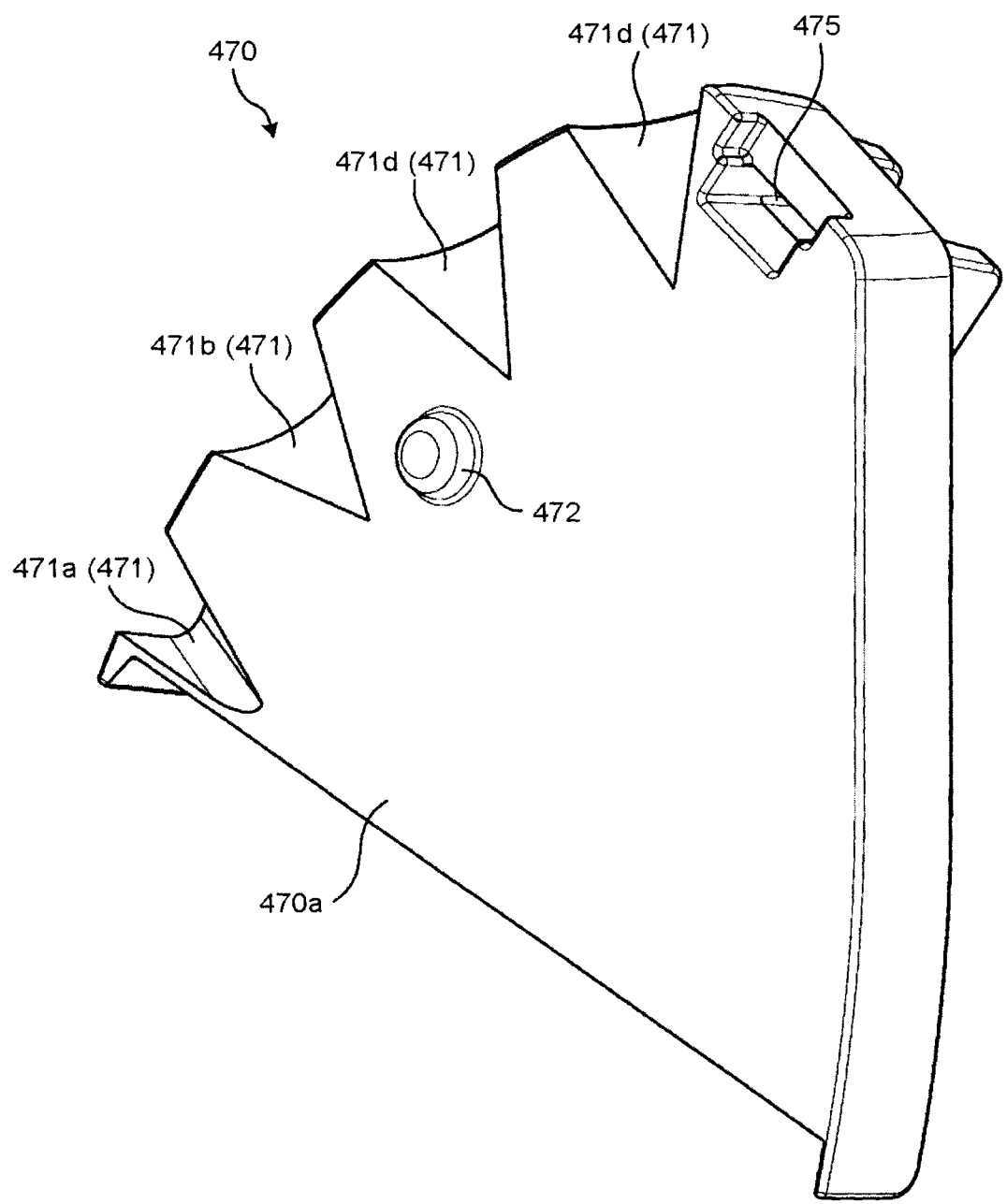
FIG. 14A is a perspective view of a guide part according to the modification of the second embodiment.
Figure 14B:
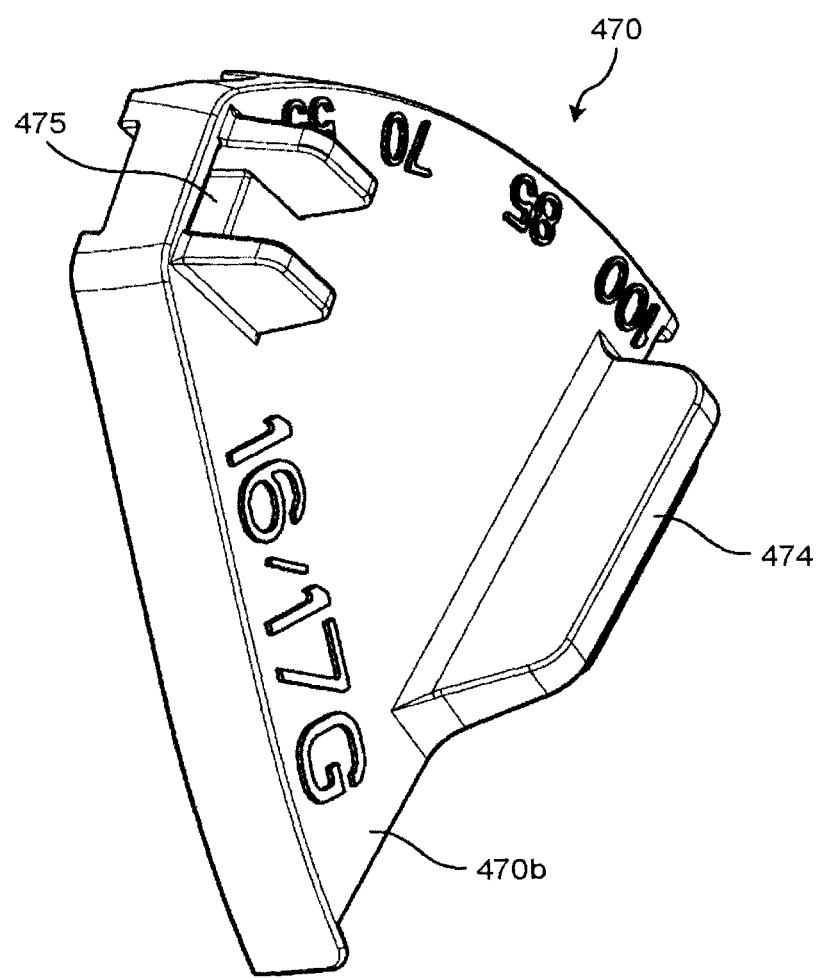
FIG. 14B is another perspective view of the guide part according to the modification of the second embodiment.

The following describes the structure of the guide part 470 with reference to FIGS. 14A and 14B. FIGS. 14A and 14B are perspective views of the guide part 470 according to the modification of the second embodiment. As illustrated in FIGS. 14A and 14B, a plurality of guide grooves 471*a*, 471*b*, 471*c*, and 471*d* that guide the puncture needle are formed on a surface (also referred to as a third surface) 470*a* of the guide part 470 coming into contact with one surface of the pressing part 480. Because the guide grooves are formed at respective positions and in respective directions, it is possible to perform a puncture on a wider area on an ultrasound image. In the following description, the guide grooves 471*a* to 471*d* are collectively referred to as guide grooves 471 unless otherwise distinguished. The surface of the guide part 470 on which the guide grooves 471 are formed is referred to as a "guide groove surface". The number of guide grooves formed on the guide part 470 is not limited to the number illustrated in FIG. 14A as long as it is the same as the number of guide grooves formed on the pressing part 480.

The guide part 470 has the protrusion 472 at a part with no guide groove formed on the guide groove surface. The protrusion 472 fits into the recess 482 of the pressing part 480. Thus, the guide groove surface of the guide part 470 is tightly attached to the guide groove surface of the pressing part 480. The pairs of guide grooves each form the inlet of the puncture needle.

The guide part 470 has the through hole 475 at an end. The connection 461 of the pressing part 480 is inserted into the through hole 475. After the connection 461 of the pressing part 480 is inserted into the through hole 475, a first hinge 491 of the fixing part 490 is also inserted therein. Thus, the connection 461 fits into the through hole 475 and engages with the first hinge 491 in the through hole 475. As a result, the connection 461 of the pressing part 480 and the first hinge 491 of the fixing part 490 are fixed.

The guide part 470 has a protrusion 474 on the surface coming into contact with the second surface 17 of the cutout portion 15. The protrusion 474 fits into the recess 19 of the cutout portion 15.

Figure 15A:
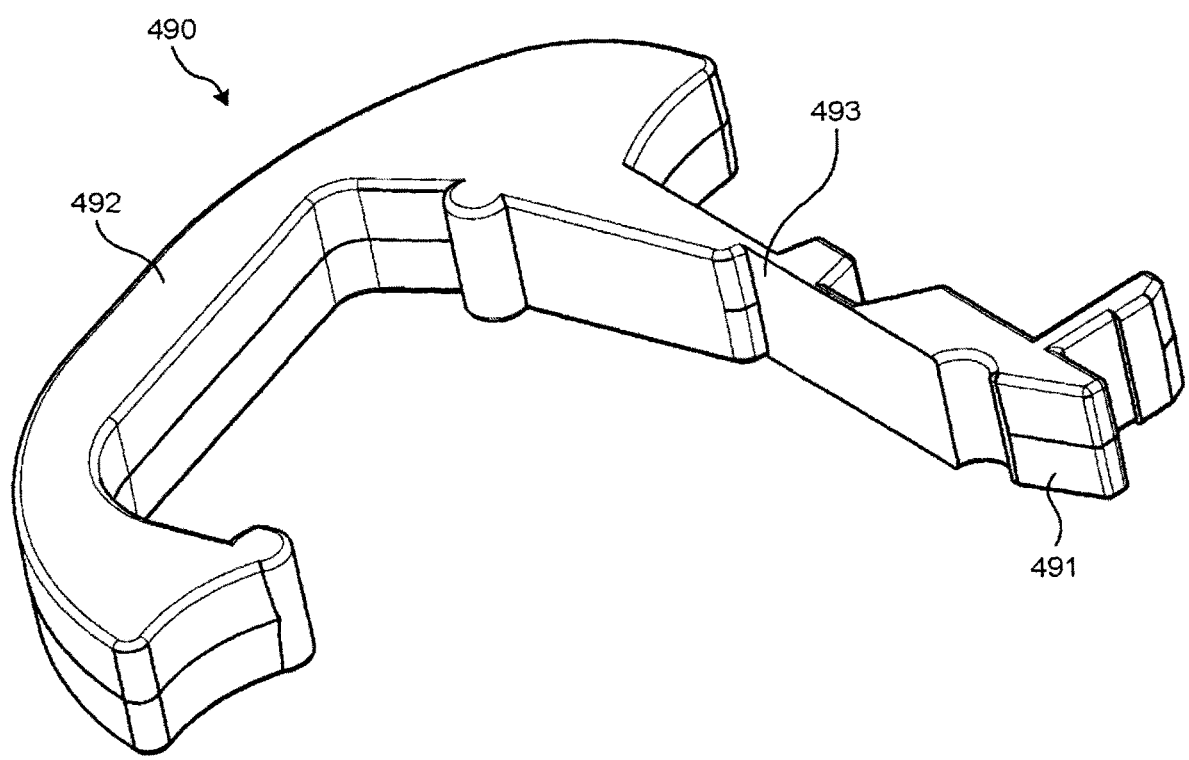
FIG. 15A is a perspective view of a fixing part according to the modification of the second embodiment.
Figure 15B:
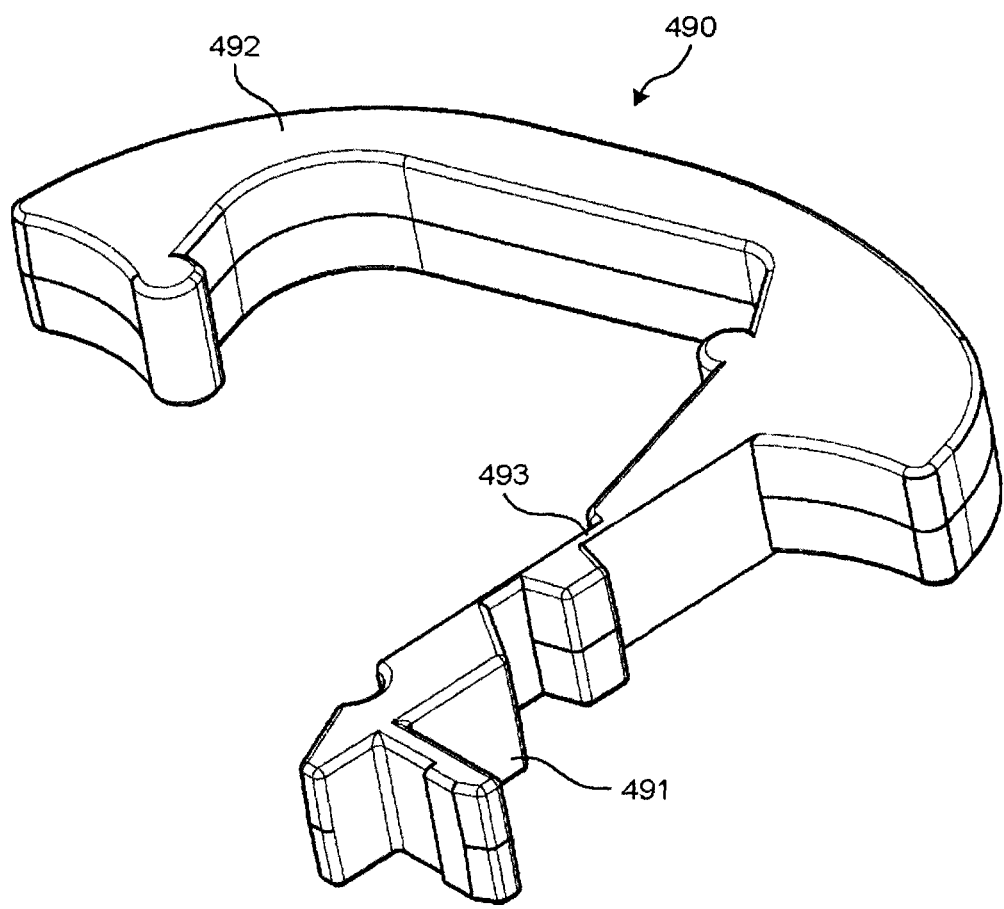
FIG. 15B is another perspective view of the fixing part according to the modification of the second embodiment.

The following describes the structure of the fixing part 490 with reference to FIGS. 15A and 15B. FIGS. 15A and 15B are perspective views of the fixing part 490 according to the modification of the second embodiment. As illustrated in FIGS. 15A and 15B, the fixing part 490 has the first hinge 491, a second hinge 492, and a coupling area 493 each of which is foldable.

The first hinge 491 of the fixing part 490 is inserted into the through hole 475 of the guide part 470 with the guide groove surface of the guide part 470 tightly attached to the guide groove surface of the pressing part 480 and with the connection 461 of the pressing part 480 inserted into the through hole 475 of the guide part 470. The first hinge 491 of the fixing part 490 engages with the guide part 470 and the pressing part 480 and is fixed. Thus, the first hinge 491 of the fixing part 490 engages with the guide part 470 and the pressing part 480, whereby the guide part 470, the pressing part 480, and the fixing part 490 are integrated. The engagement state in the through hole 475 will be described later.

The second hinge 492 of the fixing part 490 is fastened (hooked and caught) to the first surface 16 of the cutout portion 15 with the guide part 470 and the pressing part 480 sandwiched therebetween. Thus, the fixing part 490 fixes the guide part 470 and the pressing part 480 to the probe body 10 with the second surface 480b of the pressing part 480 brought into contact with the third surface 470a of the guide part 470. More specifically, a first end of the fixing part 490 (first hinge 491) is inserted into the through hole 475 with the connection 461 inserted into the through hole 475, whereby the fixing part 490 fixes the guide part 470 and the pressing part 480 in the through hole 475. When the probe body 10 is covered with the cover, a second end of the fixing part 490 (second hinge 492) is fastened to the probe body 10 with the cover interposed between the cutout surface of the cutout portion 15 and the first surface 480a of the pressing part 480 and with the surface 470a of the guide part 470 brought into contact with the second surface 480b of the pressing part 480. Thus, the fixing part 490 fixes the guide part 470 and the pressing part 480 to the probe body 10. In this case, the protrusion 474 of the guide part 470 fits into the recess 19 of the cutout portion 15, and the protrusion 486 of the pressing part 480 fits into the recess 18 on the first surface 16 of the cutout portion 15. The coupling area 493 is foldable and couples the first hinge 491 to the second hinge 492.

Figure 16:
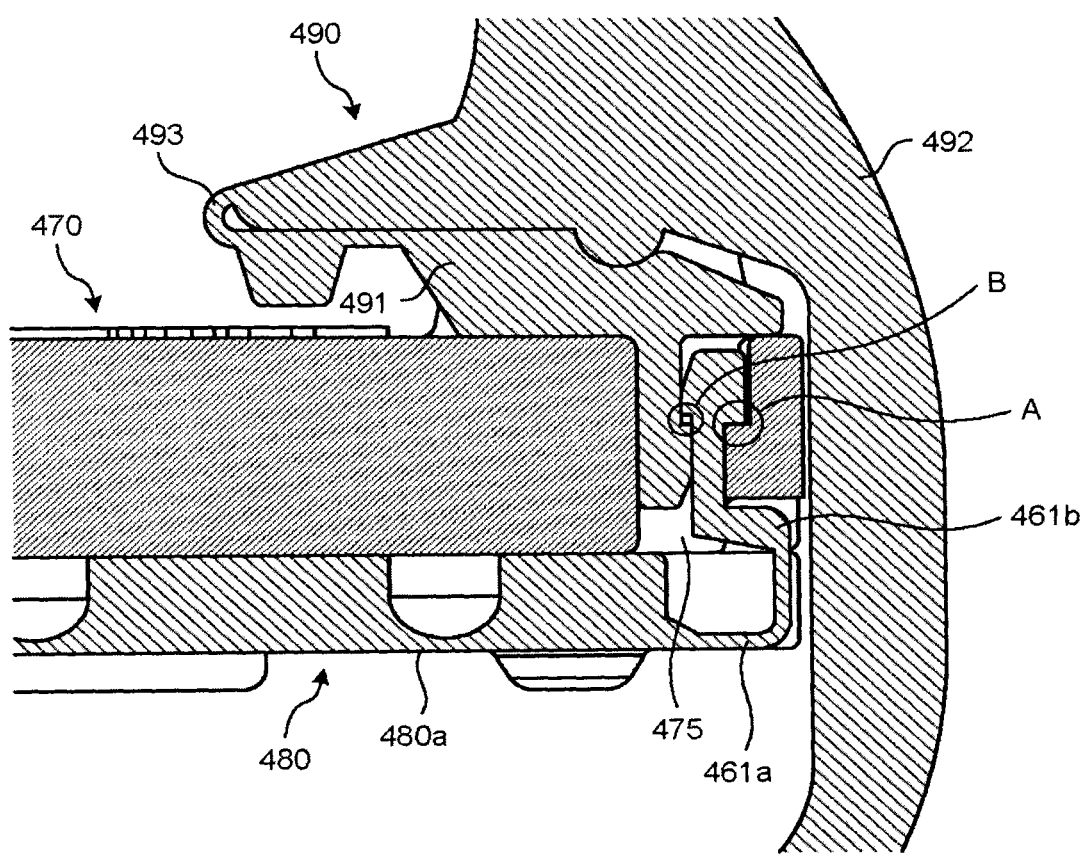
FIG. 16 is a view for explaining an engagement state in a through hole according to the modification of the second embodiment.

The following describes the engagement state in the through hole 475 with reference to FIG. 16. FIG. 16 is a view for explaining the engagement state in the through hole 475 according to the modification of the second embodiment. FIG. 16 is a top view of the adapter 460 viewed from the gripper 12 side. As illustrated in FIG. 16, the connection 461 of the pressing part 480 is inserted into the through hole 475 formed in the guide part 470, thereby engaging with the through hole 475. More specifically, the second area 461b inserted into the through hole 475 engages with the guide part 470 at A illustrated in FIG. 16. When the second area 461b engages with (is hooked and caught by) the guide part 470, the guide part 470 and the pressing part 480 are temporarily fixed and can be separated.

Subsequently, the first hinge 491 of the fixing part 490 is inserted into the through hole 475 with the second area 461b engaging with the guide part 470. Thus, the first hinge 491 engages with the connection 461. More specifically, the first hinge 491 inserted into the through hole 475 engages with the second area 461b at B illustrated in FIG. 16. The first hinge 491 engages with the second area 461b with the second area 461b engaging with the guide part 470, whereby the guide part 470, the pressing part 480, and the fixing part 490 are fixed and integrated.

The first area 461a of the connection 461 is bent, thereby bringing the second surface 480b of the pressing part 480 into contact with the surface 470a of the guide part 470. In this state, the coupling area 493 is bent, whereby the second hinge 492 sandwiches the guide part 470 and the pressing part 480. The pressing part 480 fits into the recess 18 on the first surface 16 of the cutout portion 15, and the guide part 470 fits into the recess 19 of the cutout portion 15. Subsequently, the second hinge 492 is fastened to the first surface 16 of the cutout portion 15 with the guide part 470 and the pressing part 480 sandwiched therebetween. Thus, the adapter 460 is fixed to the probe body 10. In other words, by bending the connection 461 in the state of being inserted into the through hole 475, the guide part 470 and the pressing part 480 are fixed to the probe body 10 with the surface 470a of the guide part 470 brought into contact with the second surface 480b of the pressing part 480.

In the modification of the second embodiment, the third surface 470a of the guide part 470 has the guide grooves 471, and the second surface 480b of the pressing part 480 has the guide grooves 481, for example. The guide grooves that guide the puncture needle may be formed on at least one of the third surface 470a of the guide part 470 and the second surface 480b of the pressing part 480. The third surface 470a of the guide part 470 may have the guide grooves 471, and the second surface 480b of the pressing part 480 may have no guide groove, for example. Alternatively, the third surface 470a of the guide part 470 may not have the guide grooves 471, and the second surface 480b of the pressing part 480 may have the guide grooves 481.

Third Embodiment

Figure 17:
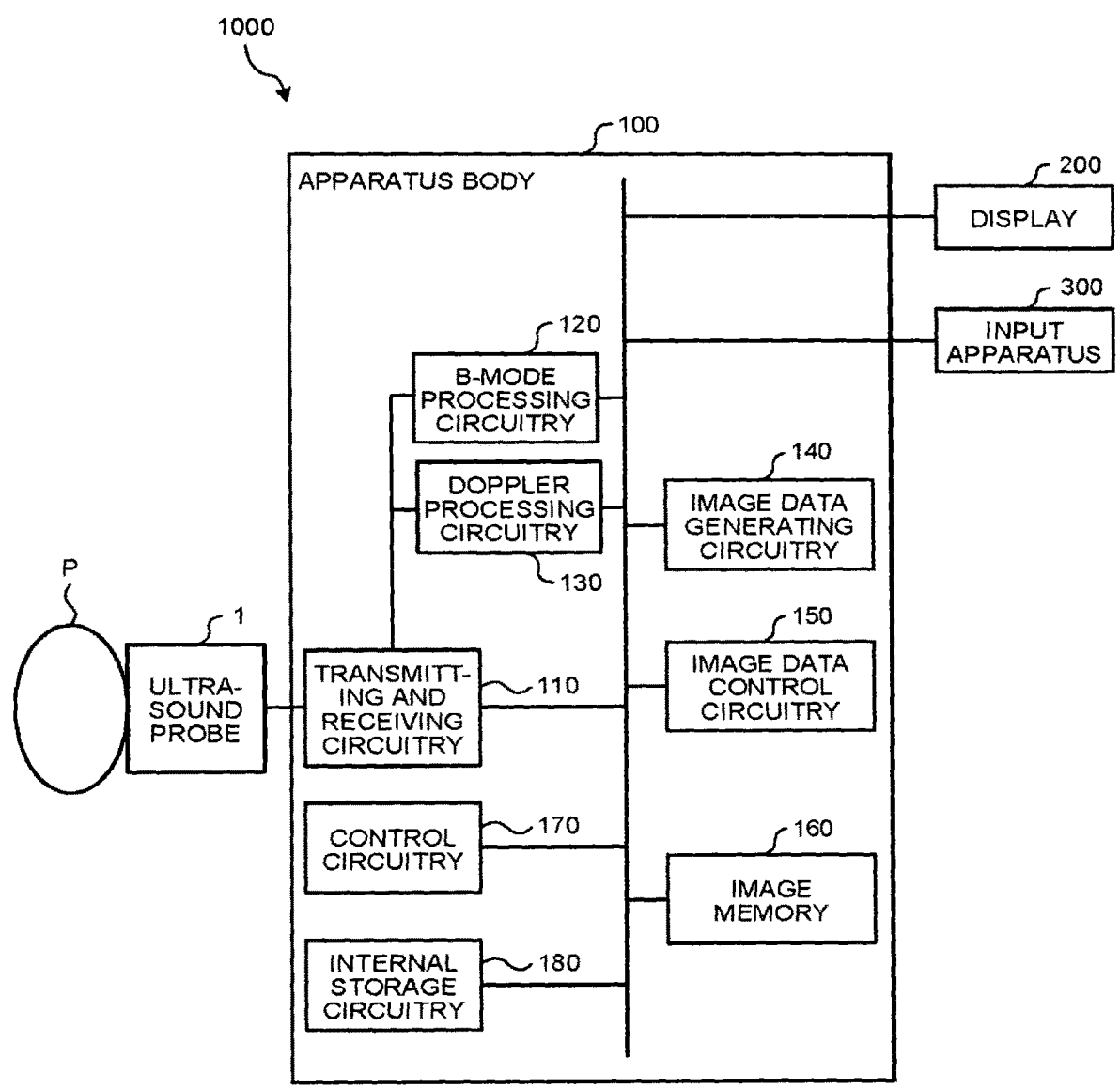
FIG. 17 is a block diagram of a configuration of an ultrasound diagnostic apparatus according to a third embodiment.

The following describes a configuration of an ultrasound diagnostic apparatus 1000 according to a third embodiment. FIG. 17 is a block diagram of the configuration of the ultrasound diagnostic apparatus 1000 according to the third embodiment. As illustrated in FIG. 17, the ultrasound diagnostic apparatus 1000 includes the ultrasound probe 1, an apparatus body 100, a display 200, and an input apparatus 300. The ultrasound probe 1 of the ultrasound diagnostic apparatus 1000 according to the third embodiment is the ultrasound probe described in the first embodiment or the second embodiment.

The ultrasound probe 1 is connected to the apparatus body 100 to transmit and receive ultrasound waves. The ultrasound probe 1 includes a plurality of piezoelectric transducer elements, for example. The piezoelectric transducer elements generate ultrasound waves based on drive signals supplied from transmitting and receiving circuitry 110 included in the apparatus body 100, which will be described later. The piezoelectric transducer elements receive reflected waves from a subject P and convert them into electrical signals. The ultrasound probe 1 includes a matching layer provided to the piezoelectric transducer elements and a backing material that prevents backward propagation of the ultrasound waves from the piezoelectric transducer elements, for example.

When the ultrasound probe 1 transmits ultrasound waves to the subject P, the transmitted ultrasound waves are sequentially reflected by a surface of discontinuity of acoustic impedance in a body tissue of the subject P. The ultrasound waves are then received by the piezoelectric transducer elements of the ultrasound probe 1 as reflected wave signals. The amplitude of the reflected wave signals depends on the difference in the acoustic impedance on the surface of discontinuity on which the ultrasound waves are reflected. The reflected wave signals may possibly be obtained by the transmitted ultrasound pulses being reflected by a moving bloodstream, a surface of a cardiac wall, or the like. In this case, the reflected wave signals are frequency-shifted by the Doppler effect depending on a velocity component of the moving body in the ultrasound-wave transmission direction.

The display 200 is a display device that displays ultrasound image data generated by the apparatus body 100. The input apparatus 300 includes an input device, such as a mouse, a keyboard, a button, a panel switch, and a trackball, and receives various setting requests from a user via the input device. The input apparatus 300 transfers the received various setting requests to the apparatus body 100.

The apparatus body 100 generates ultrasound image data based on the reflected wave signals received by the ultrasound probe 1. As illustrated in FIG. 13, the apparatus body 100 includes the transmitting and receiving circuitry 110, B-mode processing circuitry 120, Doppler processing circuitry 130, image data generating circuitry 140, image data control circuitry 150, an image memory 160, control circuitry 170, and internal storage circuitry 180.

The transmitting and receiving circuitry 110 includes a trigger generating circuit, a transmission delay circuit, and a pulser circuit, for example, and supplies drive signals to the ultrasound probe 1. The pulser circuit repeatedly generates a rate pulse to form transmitted ultrasound waves at a predetermined rate frequency. The transmission delay circuit supplies transmission delay time for each piezoelectric transducer element to each rate pulse generated by the pulser circuit. The transmission delay time is used to collimate the ultrasound waves generated from the ultrasound probe 1 in a beam-shape and determine the transmission directivity. The trigger generating circuit supplies drive signals to the ultrasound probe 1 at a timing based on the rate pulse.

The transmitting and receiving circuitry 110 includes an amplifier circuit, an analog/digital (A/D) converter, and an adder, for example. The transmitting and receiving circuitry 110 performs various types of processing on the reflected wave signals received by the ultrasound probe 1, thereby generating reflected wave data. The amplifier circuit amplifies the reflected wave signals and performs gain correction on the amplified signals. The A/D converter performs A/D conversion on the gain-corrected reflected wave signals and supplies reception delay time required to determine the reception directivity. The adder performs addition on the reflected wave signals processed by the A/D converter, thereby generating reflected wave data. The addition performed by the adder emphasizes a reflection component in a direction corresponding to the reception directivity of the reflected wave signals.

Thus, the transmitting and receiving circuitry 110 controls the transmission directivity and the reception directivity in transmission and reception of the ultrasound waves.

The B-mode processing circuitry 120 receives the reflected wave data from the transmitting and receiving circuitry 110. The B-mode processing circuitry 120 then performs logarithmic amplification, envelope detection, and other processing, thereby generating data (B-mode data) in which the signal intensity is represented by the level of luminance.

The Doppler processing circuitry 130 performs a frequency analysis on velocity information in the reflective wave data received from the transmitting and receiving circuitry 110, thereby extracting a bloodstream, a tissue, and a contrast medium echo component by the Doppler effect. Thus, the Doppler processing circuitry 130 generates data (Doppler data) by extracting moving body information, such as average velocity, dispersion, and power, at multiple points.

The image data generating circuitry 140 generates ultrasound image data from the B-mode data generated by the B-mode processing circuitry 120 and the Doppler data generated by the Doppler processing circuitry 130. The image data generating circuitry 140, for example, generates B-mode image data from the B-mode data. The image data generating circuitry 140, for example, generates color Doppler image data of an average velocity image, a dispersion image, a power image, or a combination of these images from the Doppler data. The image data generating circuitry 140 also generates M (motion) mode image data at a range gate set by the user from time-series data of the B-mode data. The image data generating circuitry 140 also generates Doppler waveform image data by chronologically plotting the velocity information on the bloodstream and the tissue at the range gate set by the user from time-series data of the Doppler data. The Doppler waveform image data is generated from the Doppler data acquired by the continuous wave (CW) Doppler method or the pulsed wave (PW) Doppler method.

The image data control circuitry 150 performs various types of processing, such as correction of the dynamic range, the luminance, the contrast, and the y curve, and RGB conversion on the ultrasound image data generated by the image data generating circuitry 140, and displays an ultrasound image subjected to the processing on the display 200. The image data control circuitry 150, for example, displays the B-mode image data generated by the image data generating circuitry 140 on the display 200. The image data control circuitry 150, for example, displays in color the color Doppler image data generated by the image data generating circuitry 140 on the display 200.

The image memory 160 stores therein the ultrasound image data generated by the image data generating circuitry 140.

The control circuitry 170 controls the entire processing in the ultrasound diagnostic apparatus. The control circuitry 170, for example, controls the transmitting and receiving circuitry 110, the B-mode processing circuitry 120, the Doppler processing circuitry 130, and the image data generating circuitry 140 based on various setting requests received from the user via the input apparatus 300, various control programs read from the internal storage circuitry 180, and various types of setting information. The control circuitry 170 displays the ultrasound image data stored in the image memory 160 on the display 200.

The internal storage circuitry 180 stores therein control programs for performing various types of processing, such as transmission and reception of ultrasound waves, image processing, and display processing, and various types of data, such as diagnostic information (e.g., a patient's ID and doctor's findings), a diagnostic protocol, and various types of setting information. The internal storage circuitry 180 is also used to retain an image stored in the image memory 160 as needed. The data stored in the internal storage circuitry 180 may be transferred to an external peripheral device via an interface circuit, which is not illustrated.

As described above, the first to the third embodiments can reduce the influence on the ultrasound effective area in a case where the probe cover is attached.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A puncture adapter comprising:
   a first pressing part configured to have a first surface and a second surface serving as a surface opposite to the first surface;
   a second pressing part configured to have a third surface;
   a fixing part configured to fix, when a probe body is covered with a cover, the first pressing part and the second pressing part to the probe body with the cover interposed between a cutout surface of a cutout portion of the probe body and the first surface of the first pressing part and with the third surface of the second pressing part brought into contact with the second surface of the first pressing part; and
   a guide groove configured to guide a puncture needle, and be formed on at least one of the second surface of the first pressing part and the third surface of the second pressing part, wherein
   the fixing part is fastened to the probe body with the first pressing part and the second pressing part sandwiched therebetween.

2. The puncture adapter according to claim 1, wherein
   the second pressing part has a through hole at an end,
   the first pressing part has a connection that is flexible at an end, and
   the second pressing part and the first pressing part are fixed to the probe body with the third surface of the second pressing part brought into contact with the second surface of the first pressing part by bending the connection in a state of being inserted into the through hole.

3. The puncture adapter according to claim 2, wherein the fixing part fixes the first pressing part and the second pressing part in the through hole by inserting a first end of the fixing part into the through hole with the connection inserted into the through hole and fixes the second pressing part and the first pressing part to the probe body by fastening, when the probe body is covered with the cover, a second end of the fixing part to the probe body with the cover interposed between the cutout surface of the cutout portion and the first surface of the first pressing part and with the third surface of the second pressing part brought into contact with the second surface of the first pressing part.

4. The puncture adapter according to claim 1, further comprising:
   a coupling part configured to be flexible, and couple respective ends of the second pressing part and the first pressing part, wherein
   the second pressing part and the first pressing part are fixed to the probe body with the third surface of the second pressing part brought into contact with the second surface of the first pressing part by bending the coupling part.

5. The puncture adapter according to claim 4, wherein the first end of the fixing part is rotatably attached to the second pressing part, and the fixing part fixes the second pressing part and the first pressing part to the probe body by fastening, when the probe body is covered with the cover, the second end of the fixing part to the probe body with the cover interposed between the cutout surface of the cutout portion and the first surface of the first pressing part and with the third surface of the second pressing part brought into contact with the second surface of the first pressing part.

6. The puncture adapter according to claim 1, wherein the fixing part comprising:
   a holding part configured to hold, when the probe body is covered with the cover, the second pressing part and the first pressing part with the cover interposed between the cutout surface of the cutout portion and the first surface of the first pressing part and with the third surface of the second pressing part brought into contact with the second surface of the first pressing part; and
   a clamp part configured to have a first end being rotatably attached to the holding part and second end, and fix the holding part by a second end being fastened to the probe body.

7. The puncture adapter according to claim 6, wherein the first pressing part comprising:
   a first thin plate part that has the first surface and the second surface; and
   a second thin plate part configured to be flexibly connected to an end of the first thin plate part, wherein
   the second thin plate part is sandwiched and fixed between the second pressing part and the holding part.

8. The puncture adapter according to claim 1, wherein
   an L-shaped cutout is formed at an end of an ultrasound wave radiation surface on which the cutout portion is formed, and
   the cutout portion has two surfaces formed along the L-shaped cutout as the cutout surface.

9. The puncture adapter according to claim 1, wherein the first pressing part includes a flange part that covers an edge of the cutout portion of the probe body when being fixed by the fixing part on at least one of an end on an inlet side of the puncture needle and an end on an outlet side of the puncture needle.

10. The puncture adapter according to claim 1, wherein the first pressing part has an average thickness of 0.1 to 0.4 mm and an average of a thickness distribution range of equal to or smaller than ±10%.

11. The puncture adapter according to claim 1, wherein the first pressing part is made of a thermoplastic resin having a tensile modulus of elasticity of 1 to 4 GPa.

12. The puncture adapter according to claim 1, wherein the first pressing part is made of any one of polyethylene, polypropylene, polycarbonate, polyacetal, and polyamide.

13. The puncture adapter according to claim 9, wherein a minimum thickness of the first pressing part is 0.1 to 0.4 mm, and a maximum thickness of the flange part is equal to or larger than 1.5 times the minimum thickness of the first pressing part.

14. The puncture adapter according to claim 1, wherein the puncture adapter is configured to be attached to the probe body when the probe body is covered with the cover.

15. An ultrasound probe comprising:
   a puncture adapter; and
   a transducer element configured to transmit and receive an ultrasound wave, wherein
   the puncture adapter comprising:
      a first pressing part configured to have a first surface and a second surface serving as a surface opposite to the first surface;
      a second pressing part configured to have a third surface; and a fixing part configured to fix, when an ultrasound probe body is covered with a cover, the first pressing part and the second pressing part to the ultrasound probe body with the cover interposed between a cutout surface of a cutout portion of the ultrasound probe body and the first surface of the first pressing part and with the third surface of the second pressing part brought into contact with the second surface of the first pressing part, and a guide groove configured to guide a puncture needle, and be formed on at least one of the second surface of the first pressing part and the third surface of the second pressing part, wherein the fixing part is fastened to the probe body with the first pressing part and the second pressing part sandwiched therebetween.

16. An ultrasound diagnostic apparatus comprising:

an ultrasound probe; and image generating circuitry configured to generate image data from a reflected wave received from the ultrasound probe, wherein the ultrasound probe comprising:

a puncture adapter; and a transducer element configured to transmit and receive an ultrasound wave, the puncture adapter comprising:

a first pressing part configured to have a first surface and a second surface serving as a surface opposite to the first surface;

a second pressing part configured to have a third surface; and a fixing part configured to fix, when an ultrasound probe body is covered with a cover, the first pressing part and the second pressing part to the ultrasound probe body with the cover interposed between a cutout surface of a cutout portion of the ultrasound probe body and the first surface of the first pressing part and with the third surface of the second pressing part brought into contact with the second surface of the first pressing part, and a guide groove configured to guide a puncture needle, and be formed on at least one of the second surface of the first pressing part and the third surface of the second pressing part, wherein the fixing part is fastened to the probe body with the first pressing part and the second pressing part sandwiched therebetween.

* * * * *